United States Patent [19]

Fuller

[11] Patent Number: 4,916,435
[45] Date of Patent: Apr. 10, 1990

[54] REMOTE CONFINEMENT MONITORING STATION AND SYSTEM INCORPORATING SAME

[75] Inventor: Kip L. Fuller, Denver, Colo.

[73] Assignee: Guardian Technologies, Inc., Cincinnati, Ohio

[21] Appl. No.: 192,216

[22] Filed: May 10, 1988

[51] Int. Cl.$^4$ .................. G08B 23/00; A61B 5/08; H04N 7/18; G06K 9/00

[52] U.S. Cl. ................... 340/573; 128/719; 358/108; 379/38; 381/42; 382/4

[58] Field of Search .......... 340/573, 576, 539, 825.49; 128/671, 719, 632, 637; 358/105, 108; 379/38, 40; 381/42; 382/3-4; 180/272; 40/21 C

[56] References Cited

U.S. PATENT DOCUMENTS

| | | |
|---|---|---|
| 3,116,365 | 12/1963 | Prescott . |
| 3,478,344 | 11/1969 | Schwitzgebel et al. ......... 340/539 X |
| 3,495,908 | 2/1970 | Rea . |
| 3,532,815 | 10/1970 | Torok . |
| 3,544,715 | 12/1970 | Herriott et al. . |
| 3,567,848 | 3/1971 | Thies et al. . |
| 3,764,270 | 10/1973 | Collier et al. ................... 128/719 X |
| 3,809,067 | 5/1974 | Hoppesch ...................... 340/576 X |
| 3,842,345 | 10/1974 | Padgitt et al. ..................... 324/71.1 |
| 3,873,771 | 3/1975 | Kleinerman et al. ................. 370/11 |
| 3,885,090 | 5/1975 | Rosenbaum .................... 358/105 X |
| 3,903,726 | 9/1975 | Hirosawa et al. ...................... 73/23 |
| 3,932,703 | 1/1976 | Bolsey ............................ 358/105 X |
| 3,970,790 | 7/1976 | Benham et al. . |
| 3,988,533 | 10/1976 | Mick et al. ........................... 358/105 |
| 4,093,945 | 6/1978 | Collier et al. ................. 340/52 R X |
| 4,136,338 | 1/1979 | Antenore ........................... 340/551 |
| 4,139,734 | 2/1979 | Fincham . |
| 4,249,207 | 2/1981 | Harman et al. ..................... 358/108 |
| 4,257,063 | 3/1981 | Loughry et al. .................... 358/108 |
| 4,445,229 | 5/1984 | Tasto et al. . |
| 4,458,266 | 7/1984 | Mahoney ........................... 358/105 |
| 4,511,886 | 4/1985 | Rodriguez ...................... 358/105 X |
| 4,549,044 | 10/1985 | Durham ............................. 379/40 |
| 4,578,539 | 3/1986 | Townsing ............................. 379/97 |
| 4,593,273 | 6/1986 | Narcisse ............................. 340/539 |
| 4,598,275 | 7/1986 | Ross et al. .......................... 340/573 |
| 4,613,845 | 9/1986 | DuBois .......................... 340/576 X |
| 4,641,186 | 2/1987 | Pritchard ............................ 358/105 |
| 4,651,144 | 3/1987 | Pagano .............................. 340/693 |
| 4,665,385 | 5/1987 | Henderson ......................... 340/539 |
| 4,670,781 | 6/1987 | Aubert et al. ......................... 358/93 |
| 4,691,340 | 9/1987 | Maeda et al. ......................... 379/96 |
| 4,706,689 | 11/1987 | Man ............................... 340/539 X |
| 4,715,059 | 12/1987 | Cooper-Hart et al. ............... 379/53 |
| 4,738,333 | 4/1988 | Collier et al. .................. 340/576 X |
| 4,747,120 | 5/1988 | Foley ................................... 379/38 |
| 4,843,377 | 6/1989 | Fuller et al. ........................ 340/573 |

Primary Examiner—Joseph A. Orsino
Assistant Examiner—Thomas J. Mullen, Jr.
Attorney, Agent, or Firm—Wood, Herron & Evans

[57] ABSTRACT

A remote confinement system is provided which includes a monitoring station having a telecommunications camera and a breath flow responsive actuating means which may form part of an alcohol breath tester. The actuating means is mounted to position the face of a person blowing thereinto facing the camera such that a properly focused, centered identifying image of consistent scale and devoid of background will be formed. Where the confinee is subject to restrictions on the use of alcohol the actuating means may form part of an alcohol breath tester which preferably has a visual display that is also included in the image field of the camera. The operation of the camera is conditioned on the commencement of the delivery of a breath sample. When a proper breath sample is provided, the camera forms and transmits at least one image to a central office by way of a communications link for interpretation. At the central office the received images are compared with file data to determine whether a specified confinee is present at the remote location where the monitoring station is located as well as the result of the breath test if one is required.

63 Claims, 8 Drawing Sheets

REMOTE CONFINEMENT MONITORING STATION AND SYSTEM INCORPORATING SAME

FIELD OF THE INVENTION

The present invention relates to verification of the identity of a particular person at a remote location, and more particularly to a monitoring station and system for verifying the identity of individuals in home arrest or remote confinement programs.

BACKGROUND OF THE INVENTION

Systems for verifying the identity of persons confined under home arrest programs and the problems associated with such identity verification are set forth in the co-pending and commonly assigned U.S. patent application Ser. No. 07/041,698 entitled "Remote Confinement System", filed on Apr. 21, 1987, which is expressly incorporated herein by reference in its entirety. That application, which on June 27, 1989 matured into U.S. Pat. No. 4,843,377, also discloses a system for remotely determining the compliance by a remotely confined confinee with behavioral restrictions associated with the confinement, including particularly the performance of unsupervised tests such as breath alcohol tests upon such a confinee along with the verification of the identity of the confinee.

The concept of remote confinement, or home arrest, is developing as a practical alternative to confinement in correctional institutions for certain types of criminal offenders. Home arrest programs are becoming increasingly popular for the purpose of relieving correctional institutions of overcrowding and reducing the cost associated with punishment by incarceration in such facilities. The development of home confinement systems requires a practical and effective method for filling the need to verify from a central office the presence of the specified confinee at an assigned remote confinement location.

In a typical remote confinement system of the type to which the present invention relates, a central office is equipped with means for selectively communicating with various remote confinement locations for the purposes of verifying the presence (identity) and optionally, the degree of sobriety of the confinees assigned to those locations. These means include a provision for selectively establishing communications links with each home confinement location. For example, provision may be made for a computer at the central office to select from a data bank the designated phone number of a specified confinee and then automatically dial, by way of a conventional telephone network, the phone number of the location to which the selected confinee is assigned.

Upon answering the telephone, the confinee is audibly prompted to identify himself or herself and optionally, to take an alcohol breath test. The confinee then takes the breath test using a portable breath tester and transmits one or more pictorial images from the remote location to the central office. These transmissions carry the visual image of the face of the confinee and optionally, the results of a breath alcohol test. Upon receipt at the central office the transmitted images may either be stored there fore subsequent identification and/or documentary or evidentiary purposes or subjected to immediate manual or automatic analysis for identification and determination of compliance with the restrictions to which the confinee may be subject including for example the requirement to be present at the remote location at certain times of a given day or restrictions on the use of alcohol. Patent application Ser. No. 07/041,698 teaches various identity confirming techniques and behavioral condition testing devices, which may be incorporated with advantage into remote confinement systems.

Identification of a person by viewing a pictorial image of a person's face is a straight forward and reliable method of identification when the identification is to be performed manually. The identification of remotely confined persons by the transmission of pictorial images is described in several of the embodiments disclosed in application Ser. No. 07/041,698.

In one prior art home confinement system employing pictorial identification, the confinee, upon being called by the central office, was instructed to place himself or herself before the camera of a picture telephone and transmit back one or more self images. Taking of these images was initiated by the confinee pressing a button on the picture telephone. If required, the timing of one or more such pictures could be arranged to include images of the confinee in the act of blowing into an alcohol breath tester as well as an image including the readout or display of the breath tester to show the result of the test. While proving quite useful and representing a significant advancement in the art, such systems are not entirely satisfactory.

First, the above systems provide no means for positively assuring the best possible camera focus and quality of transmitted images. Second, the distance between the camera and both the confinee and breath test apparatus varied depending on where the confinee chose to locate his or her person with respect to the camera. As a consequence, there was no way of ensuring that either the face of the subject or the breath tester display would be of a consistent scale. Thus, images might at times appear too small for clear reading or accurate identification. Also, the lack of a consistent camera-to-subject distance made use of automated, e.g., computerized, identification techniques much more difficult. Third, in the prior art there was no means to limit the content of the images transmitted to the central office. This is a serious shortcoming for reasons now to be discussed.

The only pictorial information legitimately required for monitoring purposes are the image of the face of the confinee and optionally, the display of the breath tester. The former image is used for identification purposes while the latter is used to indicate the result of a breath alcohol test where one is required. Because prior art systems were subject to variation in the distance between the camera and the confinees' face and/or breath tester display, the amount of "background" visible in the transmitted image could be considerable. As used herein, the term "background" in the foregoing context refers to the content of the transmitted image other than the confinee or portions of the monitoring station apparatus itself. Such background may include images of persons or things which, for reasons of privacy, should not be transmitted to the central monitoring office since they are not required to be viewed there in order to carry out the intended functions of the remote confinement system, i.e., determining that a designated confinee is present at a particular location and, optionally, determining the confinee's blood alcohol content.

The need to avoid the transmission of background and to transmit only the image of the specified confinee results, in part, from Applicant's realization that transmission of an image containing other information is socially undesirable. Surveillance of a scope extending beyond monitoring the presence and/or sobriety of the confinee might well be considered an unjustified and perhaps even illegal invasion of the constitutional rights of the confinee or others. For the same reason, a remote confinement system should not be amenable to the inadvertent or unwanted actuation of the picture taking and transmitting functions since that would be tantamount to convert surveillance. Only deliberate action on the part of the confinee should allow viewing at the central office. Accordingly, there is a need for monitoring apparatus at the remote confinement locaton which reliably ensures that only the image of the confinee necessary for identification will be subject to surveillance. It is also important that the surveillance will occur only when specifically intended by the confinee in response to an appropriate cue from the central monitoring office.

Prior art systems are subject to the inadvertent transmission of images to the central office because their image formation and transmission functions are initiated by means of a pushbutton associated with the camera at the confinement location. If the confinee presses this button when not substantially occupying the full imaging field of the camera, an intrusive transmission of background images to the central office will result. The pressing of this button by a curious or playful child has a similar effect. Accordingly, there is a need for a remote confinement system wherein image formation and transmission are not readily subject to initiation by means other than the specifically intended action of the confinee, and even if camera activation does accidentally occur, transmission of significant background will be avoided.

Prior art home arrest systems using visual identification of the confinee also lack means to provide proper lighting conditions. The formation of pictorial images which can be easily and reliably interpreted requires more predictable and uniform illumination than one can depend on to be present in varying home arrest environments. Furthermore, it is often desirable to transmit a visual image of the breath test readout. This may require lighting conditions entirely different from those required for illumination of the confinee's facial image. For example, the luminescent L.E.D. displays of the type desired and found on some available breath testers may appear "washed out" (i.e., dim or unreadable due to lack of contrast) in a pictorial image if illuminated at the relatively high levels which may be desired for producing a clear image of a confinee's face. Thus, a need exists to control the lighting conditions in connection with the transmission of images for confinee identification as well as the interpretation of breath test results in home arrest systems.

SUMMARY OF THE INVENTION

It is an object of the present invention to provide in a home arrest system the increased utility and feasibility of pictorial image methods for identifying the remotely confined confinee.

It is a further object of the present invention to provide a monitoring station for use in a remote confinement system which results in transmission of an identifiable image to the central office which is properly focused, centered, devoid of significant background information and is of a consistent linear distance scale.

It is an additional object of the present invention to provide a monitoring station for use in a remote confinement system which helps to avoid inadvertent transmission of pictorial information to the central office and helps to ensure that background information is not inadvertently transmitted even if inadvertent transmissions do occur.

It is a further object of the present invention to provide a monitoring station for use in a remote confinement system which provides proper control of lighting conditions for transmitting images of a confinee and/or the alphanumeric display of a breath alcohol tester or other device.

According to the present invention, each remote location is provided with a monitoring station which includes a telecommunications camera (picture telephone) that is capable of transmitting pictorial images over a communications link such as telephone lines. The camera has a lens which views a predetermined angular image field. The invention contemplates providing a breath flow responsive camera actuating means for causing the camera to take an identifying picture of a confinee. Where the system is to include alcohol monitoring, the actuating means preferably forms part of a breath alcohol tester. In order to initiate formation of an image and its subsequent transmission to the central office the confinee must blow into the breath inlet of the breath flow responsive camera actuating means. Further according to the invention, the relative position of the breath inlet of the breath flow responsive actuating means with respect to the field of view of the camera is such as to simultaneously satisfy several important conditions.

First, the distance from the camera lens to the face of a confinee positioned as to be capable of blowing breath into the inlet of the camera actuating means is such as to ensure a properly focused image of the confinees' face. Because this distance is a known, fixed distance, the scale of linear distance on the image can be determined. A knowledge of scale can be useful for identification purposes, particularly where automated means are used to determine whether the transmitted image suitably matches reference data identifying the confinee. Additionally, the breath inlet of the camera actuating means is positioned so that the face of the confinee (together with the display of the breath tester, if one is used) substantially fills the field of the transmitted image. This virtually precludes the chance that unduly invasive background image information will be transmitted to the central office.

The foregoing objective is further served by the fact that breath actuation is required in order to form and transmit an image. Because placing one's mouth on a mouthpiece and blowing into it is a highly volitional act, it is nearly impossible to do so inadvertently. Also, even if one (such as a child) does manage to blow into the actuating means and transmit a picture of himself, an invasion of privacy does not occur. While the image of the child will be transmitted, that image will of necessity be positioned in the field of view of the camera so as to substantially fill the image field thereby avoiding the transmission of background.

A further advantage of this arrangement is that it permits the camera to be equipped with a smaller aperture lens system. These are generally less expensive than a wide aperture system as would be required to limit transmission of background by relying solely on a shallow depth of field to selectively render background out of focus. Accordingly, the camera may be of the type having a fairly large depth of field. With the invention, the depth of field can permissibly extend five feet or more, encompassing the location where the confinee would be normally located in operation as well as what would otherwise appear in the resulting image as background without significant background being visible in the image.

To achieve the desired objectives of blocking out background images, ensuring correct focus and providing a fixed scale of distance, the breath inlet of the actuating means (which may be associated with a breath alcohol tester) may be mounted on an arm which can be either permanently fixed or fixable at a predetermined position relative to the lens of the telecommunications camera. In its operative position, the arm is positioned to locate the actuating means or breath tester such that the face of the person using the tester will be presented in proper focus to the camera. Also, the face of the confinee will substantially fill the field of view of the camera and thus substantially fill the picture image to eliminate the transmission of background information. Where a breath tester is employed, its display preferably shares the field of view with the image of the confinee so that the result of each breath test can be viewed together with the image of the confinee test subject. Forming each pictorial image with the confinee at a known distance from the camera ensures proper image focus and has the further salutary effect of preserving distance information on the image field so that a consistent distance scale for easiler identification.

Where the image formation and transmission actuating means is associated with a breath alcohol tester, further benefits are derived from the invention. The invention contemplates transmitting to the central station one or more images in response to the same flow of breath upon which the alcohol measurement is based. This has the beneficial effect of positively linking a given test result with the subject who delivered the breath sample producing that result. This deters evasion of the breath test by using a human accomplice or bogus gas delivery means, such as a balloon, since the image of the accomplice or bogus apparatus would be visible in place of the designated confinee.

Where more than one image is transmitted, as in the preferred embodiment to be described, at least one such subsequent image is automatically formed and transmitted following a time delay after the flow of breath above a predetermined rate has commenced. If the flow of breath has not been maintained continuously without interruption, at at least the predetermined flow rate, the breath tester display so indicates by means of an appropriate "abort" message. Alternatively, the transmission of the subsequent image could be disabled so that failure to receive it at the central office would indicate an abort condition. The time interval and predetermined minimum sufficient flow rate are selected in the manner known in the art to require a "deep lung" sample of breath as is required for a valid breath alcohol measurement. The second image is preferably also formed at a time when the numerical result of the breath test appear on the breath tester display in order to communicate the result of the breath alcohol test to the central office. Thus, means are provided not only to ensure that the breath test is an accurate one based on a deep lung breath sample but also to communicate the breath test result. In so doing, the invention further provides plural, time-spaced images of the confinee in the act of delivering the sample. The invention thereby further deters attempts to evade the breath test by providing assurance that the depicted confinee has continuously remained in the position required to deliver a breath sample thereby precluding the possibility that an accomplice or bogus gas supply could have been substituted for the confinee after the first image was formed. Thus, the indicated result of the breath test reliably represents the condition of the individual depicted in the images.

In one preferred embodiment of the present invention, two time-spaced pictorial images are formed and transmitted to the central office. The first image is that of the face of the confinee and the display of the breath tester disposed closely adjacent thereto and is provided for primary identification. In forming this image, the confinee's face is illuminated by a lamp provided on the monitoring station which is lighted in response to the delivery of a breath sample. A second image is of identical composition as the first (i.e., including the face of the confinee and the display), but is taken at a later time when the numerical results of the breath test have appeared on the breath tester display. This second image is formed without illumination by the lamp, but only with the self-illumination of lighted characters of the breath tester's display so that the display is clearly readable.

These and other objectives and advantages of the present invention will be more readily apparent from the following detailed description of the drawings in which:

DETAILED DESCRIPTION OF THE INVENTION

Figure 1:
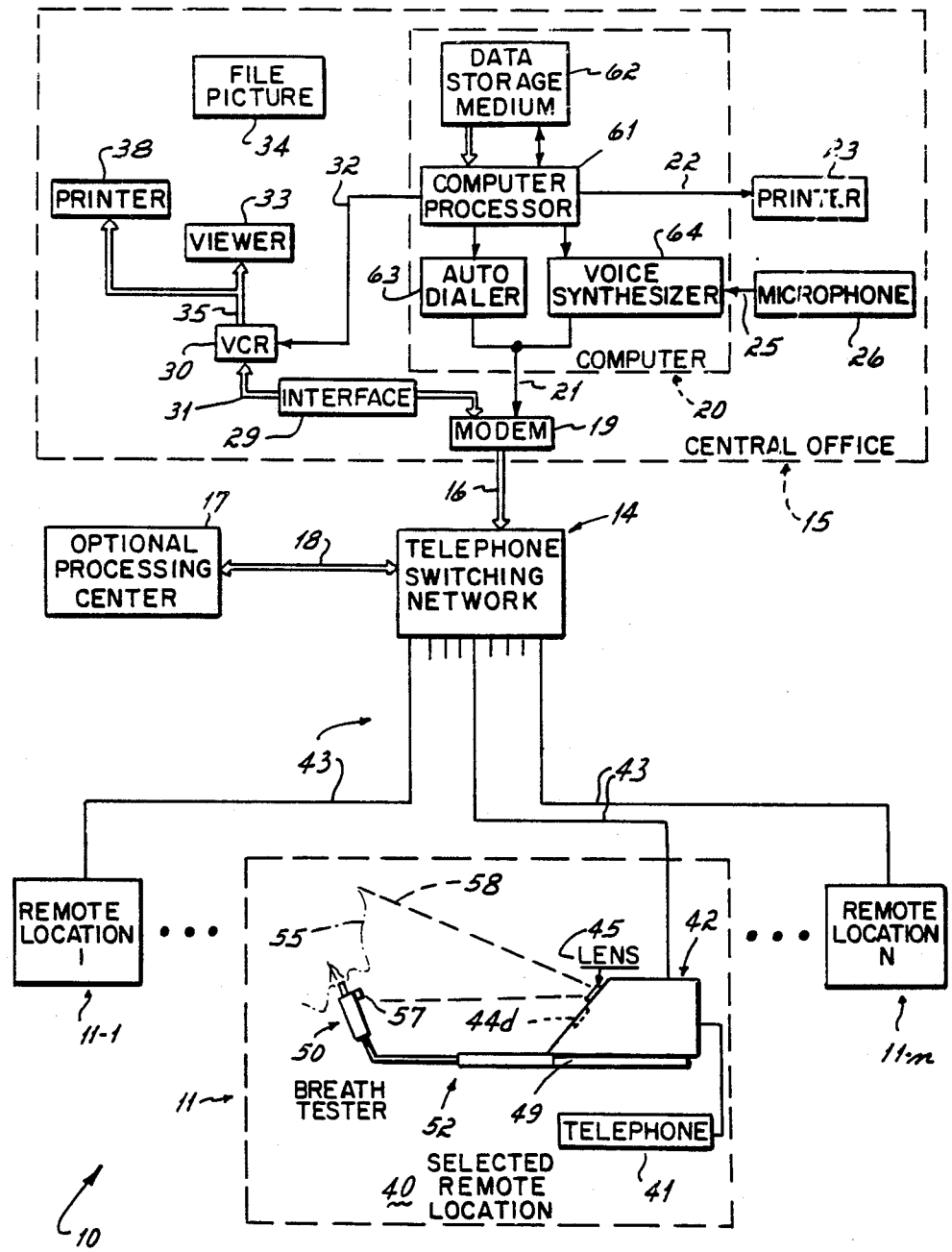
FIG. 1 is a block diagram of one embodiment of a remote confinement system incorporating the monitoring station of this invention.

Referring to FIG. 1, a remote confinement system 10 is illustrated which incorporates the monitoring station of this invention. The system 10 includes a plurality of remote confinement locations 11, represented in FIG. 1 as 11-1 through 11-n. The locations 11 represent the homes or other remote confinement locations to which confines are assigned or sentenced in a home incarceration program. Each of the locations 11 is provided with a connection to a conventional telephone line 43 which extends from the locaation 11 to a telephone switching network 14 of a conventional telephone system.

The remote confinement system 10 includes a central office 15 which is provided with equipment and personnel for monitoring confinees at the individual remote locations 11. The remote locations 11 are usually (but not necessarily) geographically spaced from one another as well as from central office 15. The equipment at the central office 15 is capable of monitoring a plurality of the remote locations 11 which preferably lie within the local calling area of the central office 15.

Central office 15 provides means for the automatic selection of a specified confinee for a scheduled or semirandom monitoring call, the automatic dialing of the telephone number of the remote location 11 to which the selected confinee is assigned in order to establish a telephone communications link through the network 14 to the selected one of the remote locations 11, the transmission of a prerecorded or synthesized audible instruction message to the confinee over the established communications link, and optionally, the recording of information received through the communications link from the selected one of the remote locations 11 in response to the acts of the selected confinee performed in response to the communicated message. The central office usually also includes personnel or other means to interpret the transmissions received in response to its calls to determine whether a violation has occurred. This consists fundamentally of determining whether a responding transmission is received when the confinee is required to be present at the remote location and if so, whether the content of the transmission indicates that the designated confinee is present. This is done by comparing the transmitted image with file data which may be stored and retrieved in physical form such as photographs or electronically. If the confinee is subject to restrictions on the use of alcohol, the results of a breath alcohol test are interpreted. When a violation is determined to have occurred it is logged and if appropriate, reported to proper authorities either immediately or some later time as circumstances warrant.

The central office 15 is connected through a conventional telephone line 16 to the telephone switching network 14 of the telephone system. In accordance with optional features of the present invention as will be described in more detail below, the system 10 may be provided with a processing center 17 having functions similar to those described above for the central office 15, but located remotely therefrom. Where employed, processing center 17 is connected to one or more individual central offices 15 by a second communications link which may be established for example by connection to the local telephone network 14 through a long distance telephone communications link 18.

Referring more particularly to FIG. 1, the central office 15 is equipped with a computer 20 whose general operation is described hereinafter with reference to FIG. 7. Computer 20 may comprise a general purpose personal computer such as an IBM PC XT and is preferably equipped with a hard disk storage media. Computer 20 includes a serial output port 21 of the conventional RS-232C type, connected to the telephone line 16 via a modem 19. The computer 20 is also provided with a standard parallel output 22 connected to a printer 23 which is provided to print out a hard copy of a log of monitoring operations. The computer 20 is further provided with a resident voice synthesizer to which a microphone 26 is connected by way of an input connector 25 for use in generating prerecorded messages. Optionally, the central office 15 is equipped with a video cassette recorder 30 (VCR). The VCR 30 is connected via an interface printed circuit board 29 and a video input-output cable 3 to the telephone line 16. A control input cable 32 connects a control output port of the computer 20 to the control input of the VCR 30. A monitor screen or viewer 33 is also provided at the central office 15. Viewer 33 provides means for visual comparison of pictorial images received over the phone line 16 with a corresponding file picture 34 of the confinee retrieved from storage in a file. The viewer 33 is connected to an output 35 of the VCR 30. While a photograph retrieved from a physical file may serve the purpose, the images comprising file picture 34 may optionally be stored in digitized form accessible via computer and displayed electronically on a screen. It may be preferable in some applications to store the file information in other than digitized or hard copy form. In such cases pictorial images to be utilized as identification references in the system 10 can be maintained in analog form, may be stored on a video cassette for screen display. A printer 38 is also provided at the central office 15 for printing hard copies of the images sent through output line 35 to viewer 33. The printer 38 is provided with an input cable connected from the line 35. All of the hardware and supporting software utilized at central station 15 is commercially avaliable from Luma Telecom, Inc. of Santa Clara, Calif. as part of its Luma Interactive Monitoring System (LIMS).

It is of course possible to use other than a standard telephone exchange as a communications link. In such a case, the data storage medium 62 will contain whatever information is necessary and appropriate to enable the computer 20 to establish a communications link to the selected remote location 40 through the network employed. Additionally, it may be desirable to use information other than the pictorial image of a person for purposes of identification. Those skilled in the art will appreciate that alternate forms of visual identification such as fingerprinting or retinal vasculature imaging may also be suitably adapted for use with the invention. Moreover, the identifying information need not be stored in humanly readable form. Instead, file picture 34 or other identifying data can be stored electronically in analog or digital form and, if necessary, transcribed by electronic means to humanly readable form.

The equipment at the central office 15 operates to select a specified confinee and to establish a communications link to the equipment at the remote location 11 at which the selected confinee is assigned. In the preferred embodiment, a telephone communications link is used. Computer 20 includes an auto dialer 63 to call selected remote locations 11 as monitoring circumstances warrant. Calling schedules may be arranged on any desired basis including a periodic one but are preferably arranged on a random or pseudo-random basis to avoid a high degree of predictability by the confinee. Provision may be made in the schedule to avoid calling a particular confinee at times when that person may be permissibly absent from their assigned remote location for legitimate reasons such as going to work.

A selected one of the remote locations 11 to be called at a given time is illustrated in FIG. 1 as selected remote location 40. Each remote location 11, including selected remote location 40, is provided with a telecommunications camera (picture telephone) 42 which is connected to a telephone line 43. The telecommunications camera 42 may be one of a number of suitable types. One such device which is commercially available is marketed under the trademark Visitel and is manufactured by Luma Telecom, Inc. of Santa Clara, Calif., a subsidiary of Mitsubishi Electric Sales America, Inc. The Visitel camera is connectable directly to a standard voice grade telephone line 43 and includes a camera and supporting circuitry which, when actuated, form a still pictorial image of objects within the field of view of its lens, and then serially transmit the image onto a telephone line. A complete image formation/transmission cycle takes approximately five seconds. The Visitel camera 42 connects directly to the telephone line by way of a Y-cable 12 having a modular telephone jack plug (not shown) for connection to the telephone line 43. The Y-cable 12 also includes a power connector comprising an AC to DC converter unit which may be plugged into a conventional 115 Volt AC wall outlet. For audio communication, a conventional telephone 41 plugs into a modular output jack.

For the purposes of the present invention, the telecommunications camera 42 does not require all of the features of the commercially available Visitel unit. For example, user accessible pushbuttons 44 which are provided on the commercial Visitel product to initiate forming and transmitting an image are removed and circuitry is added to interface the camera with a breath alcohol tester to adapt unit 42 for use with the present invention as described in further detail later.

Figure 2:
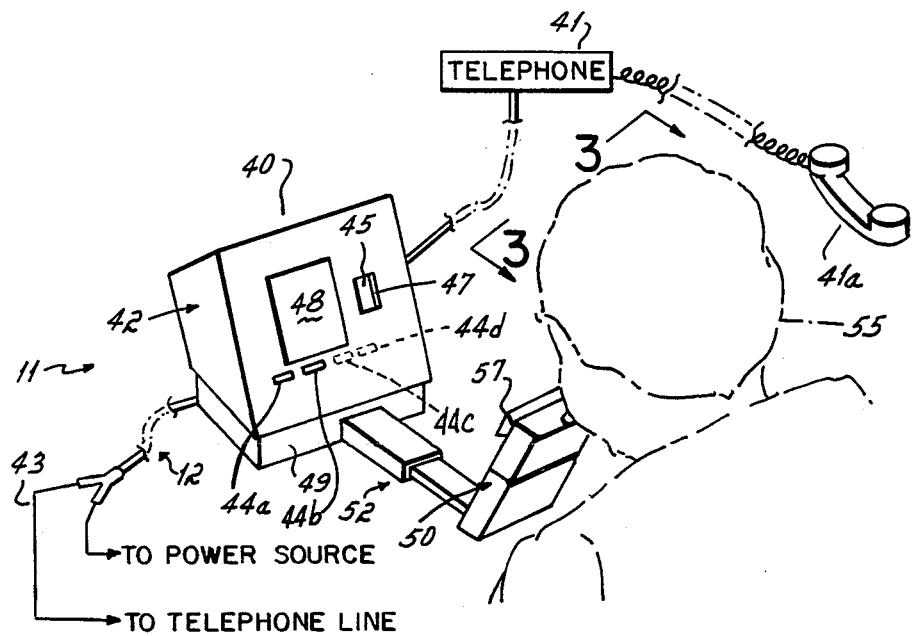
FIG. 2 is a perspective view of one embodiment of the monitoring station of the present invention.

As illustrated in FIG. 2, the camera lens 45 is provided with a sliding lens cover 47, which is connected to certain enabling switches described in more detail below. Advantageously, a camera lamp 48 is added to the standard Visitel unit in order to adapt it for use with the invention for adequately and uniformly illuminating the face of a person to be viewed by the camera 45 regardless of ambient lighting conditions. Camera lamp 48 may comprise a conventional 120 Volt, 30 watt miniature spot lamp.

The standard Visitel unit currently being sold commercially by Luma Telecom, Inc. includes a CRT which provides a real time video display of the image within the field of view of camera 42 so that a user can properly pose and be centered in the field of view before transmitting an image. Since arm 52 acts to properly position a user within the image field of camera 42, the CRT is not necessary and is therefore preferably removed. Lamp 48 is conveniently mounted behind a transparent or translucent panel on the front panel of the camera 42 in the area from which the CRT has been removed and is directed toward the tester 50 so as to control the level of illumination of the face of the person 55 when a picture is being taken through the lens of the camera 42.

Figure 4:
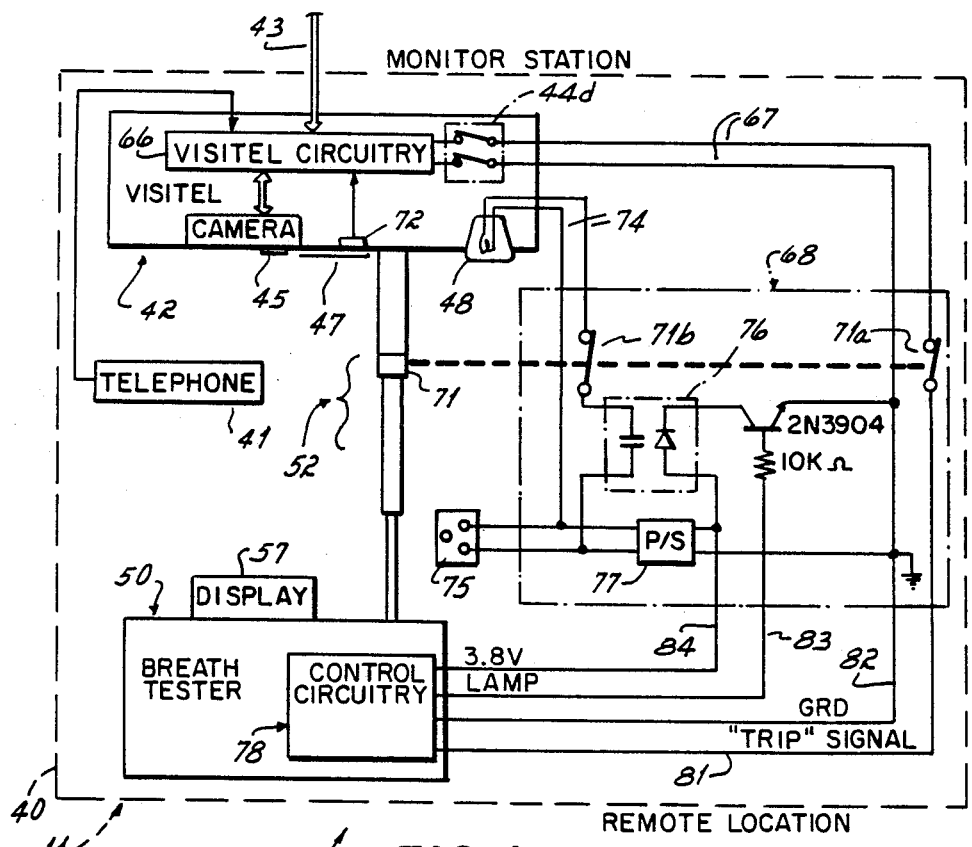
FIG. 4 is an electrical diagram of one preferred embodiment of a monitoring station according to the present invention.

Referring now to FIG. 2 and FIG. 4, the standard Visitel product adapted to comprise telecommunications camera 42 also includes a series of four user-accessible push buttons 44a–44d to control its operation. These include a "BRIGHT UP" push button 44a for brightening the image, a "BRIGHT DOWN" push button 44b for darkening the image, a "VIEW POSE" push button 44c (whose function is not relevant here) and a "SEND" push button 44d. "SEND" push button 44d initiates the forming and transmission of an image. Push buttons 44c and 44d are removed from the front panel of the Visitel unit 42 so as not to be externally accessible while push buttons 44a and 44b are preferably left in place. The internal electrical connections to push button 44c are disconnected and permanently wired to remain in the state corresponding to the normal, unactuated switching state of push button 44c. The switch contacts of push button 44d are connected via jumper wires 67 to connect the camera circuitry 66 to a controller circuit board 68 which can be conveniently mounted in the base 49 of the telecommunications camera 42. As will be explained further, the above modifications serve the important function of linking the "SEND" function to the breath alcohol tester 50 so that the forming and transmission of a pictorial image by camera 42 can be initiated only in response to delivering a breath sample into breath tester 50.

Figure 5:
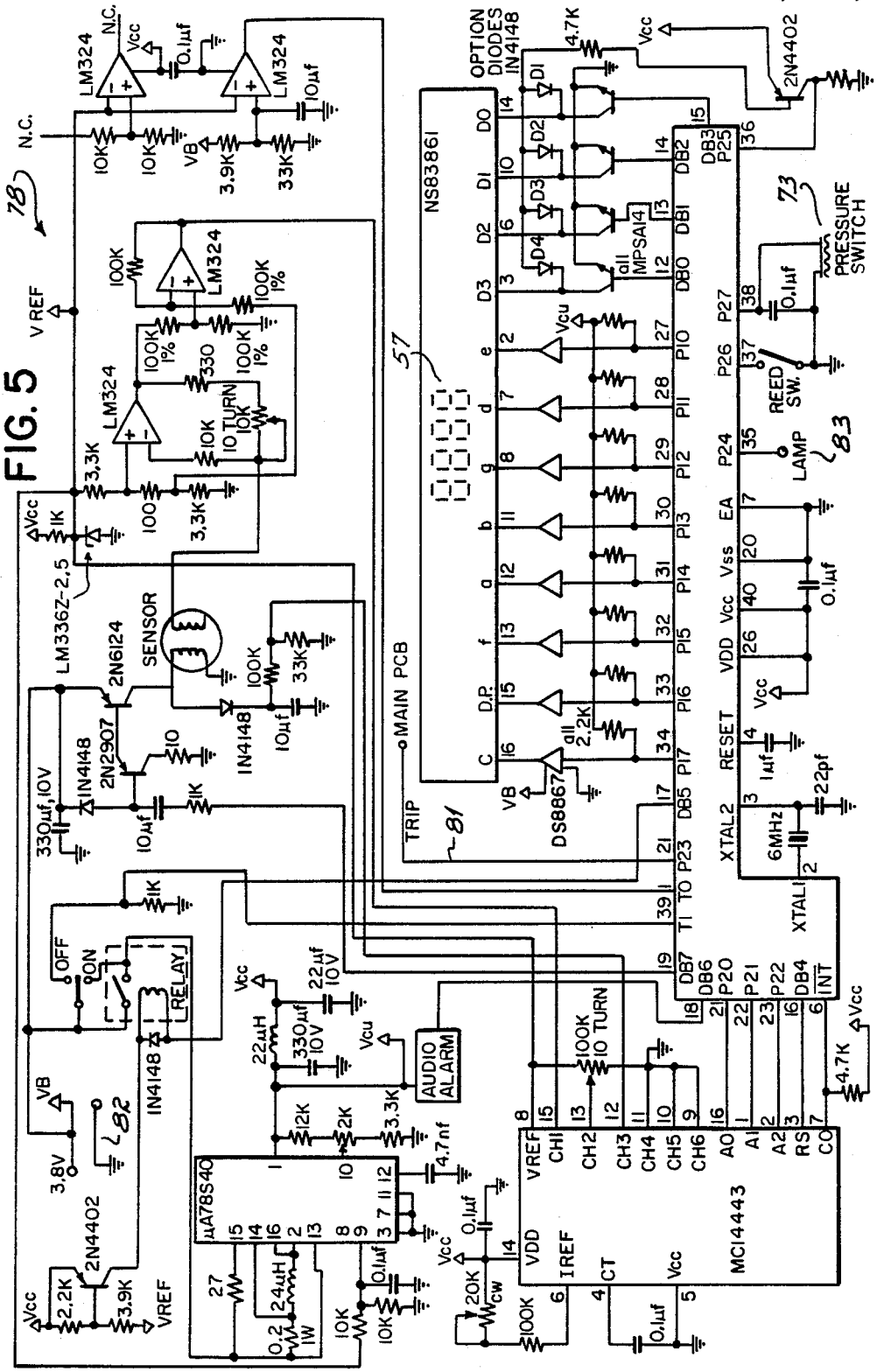
FIG. 5 is an electrical schematic diagram detailing the control circuitry of the breath tester shown in FIG. 4.

Each remote location 11 is provided with breath responsive actuating means for triggering camera 42 to form and transmit images. To facilitate alcohol breath testing of confines, this actuating means preferably forms part of breath alcohol tester 50. The tester 50 preferably comprises a modified Alert model J-4 which is commercially available and is manufactured by Alcohol Countermeasures Systems, Inc. of Mississauga, Ontario, Canada. For purposes of the present invention, it should be appreciated that breath tester 50 includes flow sensing means such as a pressure switch which closes when a user blows into the tester mouthpiece to signal the delivery of a breath sample. Breath tester 50 further includes an alcohol sensor such as a Figaro Engineering Co. Model TGS109 Tin Oxide Semiconductor Gas Sensor which measures the alcohol content of the sample, a four digit display for displaying an alcohol reading to the camera, and circuitry containing electronics and software to support the operation of the alcohol sensor and the display. These components are shown in FIG. 5, described below and in connection with the flow charts of FIGS. 6A–D. In the preferred embodiment, the standard circuitry and software of the model J-4 breath tester are modified slightly to perform the additional functions described in connection with the schematic of FIG. 5, to interface with the other circuitry of camera 42 and to operate in accordance with the flow chart of FIGS. 6A–D below.

The monitoring station illustrated at the selected remote location 40 is representative of the equipment at each of the remote locations 11. Its external physical configuration is illustrated in both FIGS. 1 and 2. In FIG. 2, the camera 42 connected to breath tester 50 as described above is illustrated connected via a Y-cable 12 to both the telephone line 43 and a power source as previously described. A standard telephone 41 having a handset 41a (or conference type remote speaker and microphone) patches into telephone line 12 by way of a standard phone cord having a modular jack plug (not shown) receivable in an appropriate jack in the rear of camera 42.

Breath tester 50 is supported on an arm 52 which extends from a base 49 disposed beneath the camera 42. The arm 52 supports the tester 50 for operation at a predetermined distance and position in relation to the lens 45 of the camera 42. Camera 42 is physically situated so that its lens 45 directed and focused to form a clear image of the face of the person 55 positioned at this predetermined location. As shown in FIG. 2, the correct positioning of the person 55 at this predetermined location results when the confinee 55 is using the breath tester 50 by blowing into its mouthpiece. The proper relationship between camera 42 and the face of the person 55 is established by the geometry of the arm 52 which preferably supports breath tester and which preferably is mounted to the base 49 which supports camera 42. The arm 52 may comprise a structure having a fixed effective length and height or may comprise a structure selectively extendable along one or more such axes as is the telescoping arm 52 as shown in FIGS. 1 and 2. Arm 52 has a height and a maximum extended length in its fully extended position (as shown) which will position the tester 50 as to locate the breath inlet mouthpiece of the tester 50 in a predetermined location. This location is selected so that when a user positions himself or herself to blow into the mouthpiece of tester 50 the use and breath tester are located within the image field of camera 42. Arm 52 preferably includes an outwardly angled section adapted to present the mouthpiece of breath tester 50 at an angle with respect to the mouth of the user so that the user can look straight into the lens 45 of camera 42 while blowing into breath tester 50. Further, the face of the user 55 together with the display 57 of tester 50 substantially fills the image field 58 (FIG. 3) of camera 42 and are laterally centered therein to thereby preclude transmission of undesired background information. The horizontal distance from the lens 45 of camera to the face of the user 55 is selected in accordance with the focal distance and depth of field of camera 42 so as to present the face of the user in proper focus. Thus, the geometry of arm 52 affords both a readable image of display 57 without including significant visible background images.

It can readily be appreciatd that arm 52 need not be permanently physically connected to either camera 42 or breath tester 50 to perform the above functions but can be detachable from either so long as means are provided to permit arm 52 to be placed as to properly and repeatably position the breath inlet of tester 50 relative lens 45 in the required manner described above. Moreover, while desirable for unobtrusive storage between uses, arm 52 need not be telescoping or collapsible but may comprise a member of substantially fixed dimensions. Where the arm 52 is of the telescoping type, it is perferably provided with a limit switch 71 which will enable camera 42, when actuated, to operate to take a picture and to transmit an image only when arm 52 is fully extended thereby ensuring properly focused images devoid of objectionable background. Similarly, the lens cover 47 which covers the camera lens 45 actuates another switch 72 which permits the taking of a picture and transmission of the image only when the lens cover 47 is opened. If a limit switch sensing the extension of arm 52 is employed, its contacts may conveniently be wired electrically in series with those of the switch associated with lens cover 47.

Breath tester 50 is provided with a visual alphanumeric display 57 for reading out the results of the breath test. As previously noted, the display 57 is positioned by arm 52 so as to be readable within the image field 58 defined by camera 42. The display 57 of the model J-4 breath tester is a 4 digit, 7 segment, L.E.D. type display providing illuminated figures which are readable visually. Accordingly, an image including display 57 is effective to transmit the information contained thereon to the central office 15. However, the formation of this image is preferably done without additional illumination by the lamp 48 which would tend to "wash out" the display 57 and render the image generated by camera 42 unreadable.

Figure 3:
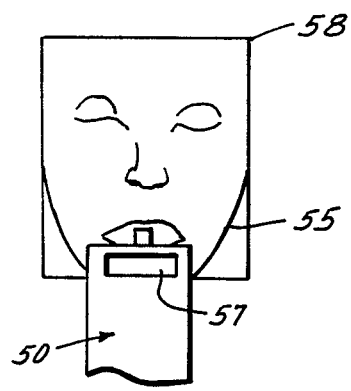
FIG. 3 is a view along line 3—3 of FIG. 2 from the camera lens toward the confinee showing the position of the face of the confinee with respect to the image field of the camera.

The image field which bounds the picture taken through the lens 45 of camera 42 is illustrated in FIG. 3 by the lines 48 which define the perimeter of the field and transmitted image at the point when arm 52 is in its operative or fully extended position. The predetermined distance maintained by the arm 52 is such that the boundary of the formed pictorial image of the face of the person 55 will define an area of the person's face so that the face and display substantially fully fill the formed pictorial image. This is more specifically illustrated by FIG. 3. The perimeter of the image field of camera 42, as illustrated by the line 58, preferably falls slightly within the perimeter of the facial image of the person 55. Image field 58 is also just large enough to include the display 57 of the tester 50.

Because its size is known, display 57 provides a convenient linear distance reference disposed adjacent the image of the face of the person 55 so as to facilitate the identification process. Even without the presence of display 57, the fact that arm 52 predetermines the dsistance between camera lens 45 and the face of the person 55 when an image is formed provides knowledge of the scale of linear distance on the images. This is particularly advantageous for the requirements of automated image identification where that is desired. A further advantage of the maintenance of full field image in this manner is the elimination of unwanted background which might include images of persons other than the specified confinee or objects in the confinee's household. As noted previously, transmission of such background to the central office is to be avoided in order to minimize the degree of intrusion that monitoring requires.

When called by central office 15 a person 55 at remote location 40 hears a synthesized instruction message on handset 41a upon answering telephone 41. The person responds by simultaneously initiating both a breath test and the transmission of a pair of pictorial images using breath alcohol tester 50 linked to camera 42 as described herein to form the remote monitoring station. To use the monitoring station to respond, the confinee 55 pulls tester 50 away from the camera 42 to withdraw telescoping arm 52 to its fully extended position. When arm 52 if fully extended as shown in FIGS. 2 and 4, an arm extension limit switch 71, which is normally open, closes. Limit switch 71 is a double pole limit switch having poles 71a and 71b connected as shown in FIG. 4 to partially enable camera 42 so it can form and transmit an image only when arm 52 is fully extended. This is achieved by connection of the switch section 71a in series with the jumper wires 67 connected to the contacts of the SEND push button 44d which has previously been removed. Pole section 71b is connected in series with the hot line of a single phase 115 volt a.c. cable 74 which connects the lamp 48 with a 3-prong grounded male line plug 75. The cable 74 and the jumper wires 67 are connected to the plug 75 and breath tester 50 through the controller circuit board 68 which may conveniently be housed within the base 49 disposed beneath camera unit 42. Board 68 includes an optically isolated electronic relay 76 having normally open contacts connected in series with switch pole 71b as shown.

A 3.8 volt D.C. power supply 77 is also provided on the circuit board 68 to provide power to tester 50 and relay 76. The power supply 77 has an input connected across the 115 volt A.C. line from the line plug 75. The 3.8 volt positive D.C. output of the power supply 77 connects to the power terminal of the tester 50 and to one side of the input of relay 76. As long as the AC power cord of camera 42 remains plugged into an energized outlet, breath tester 50 is supplied power via circuit board 68 to maintain a constantly powered-up, ON condition. This allows tester 50 to be ready for use without a warm up period which would otherwise be required in order to purge its alcohol sensor. Power supply 77 is also connected to the collector of a 2N3904 switching transistor whose emitter is grounded and whose base is connected through a 10K ohm resistor from the LAMP signal output terminal of tester 50 as desscribed below in connection with the description of the control circuitry 78 illustrated in FIG. 5.

Once arm 52 is fully extended, the user slides the slidable lens cover 47 to its open position. A second limit limit switch 72 is thereby actuated to then fully enable the camera activation camera circuitry 70. The confinee 55 then performs a breath alcohol test by placing his mouth upon the mouthpiece of the tester 50 and then exhaling into it continuously without interruption for at least about five seconds.

The design and operation of alcohol breath testers is discussed in detail in various patents and other prior art publications including U.S. Pat. Nos. 3,764,270 and 4,093,945 and therefore, needs no detailed explanation here. In summary, these patents show that an accurate measurement of a person's blood alcohol content can be made by measuring the alcohol in air sampled from the alveoli of the lungs. Such a sample is obtained by requiring the person tested to exhale a deep lung sample of breath which is obtained by blowing into the mouthpiece of the tester at at least a minimum sufficient flow rate for at least a minimum interval of time. In the J-4 breath alcohol tester, this interval is slightly in excess of five seconds. Accordingly, when a breath sample is delivered, a pressure switch 73 (FIG. 5) which is a standard component of the model J-4 tester closes to signal that the delivery of a breath sample at at least a minimum prescribed flow rate has begun. The continuous delivery of the breath sample causes pressure switch 73 to remain closed as do switches 71 and 72, to add a further required condition for activation of the control circuitry 66 of camera 42. When all the necessary conditions signalled by switches 71, 72 and 73 are satisfied, camera 42 is energized in order to form an image which includes a sufficient portion of the face of the user 55 of breath tester 50 to permit identification of the person, the readout or display of breath tester 50 and substantially nothing else in the background. To fully and uniformly illuminate the user's face to permit formation of a clear image thereof regardless of ambient light levels, at least one image is preferably formed while the user's face is illuminated with light from lamp 48. Camera 42 automatically transmits the formed image to central office 15 by way of telephone line 12. If the image received at the central office is either too bright or too dark, the confinee can be instructed via telephone 41 to press the appropriate BRIGHT DOWN or BRIGHT UP push button (44b and 44a respectively) to correct the problem and then instructed to repeat the identification procedure.

Where breath alcohol testing is required, at least one additional image is preferably formed and transmitted substantially contemporaneously with the breath test. This image shows the face of the user of the breath tester as well as the result of the test as it appears on display 57. So that display 57 is clearly readable, the latter image is preferably formed without lamp 48 being illuminated.

The control signals which actuate the operation of camera 42 through the lines 67 and 74 are generated by the circuitry 78 of the breath tester 50, the schematic of which is illustrated in FIG. 5. This circuitry 78 is the standard circuitry provided with the commercially available Alert J-4 tester with the following modifications: First, the conductor from pin P23 of the D8749H microprocessor is interrupted and P23 is connected through a TRIP signal conductor 81 on circuit board 68 and a pole section 71a of limit switch 71 to a terminal of the SEND switch 44 of the VISITEL camera 42; the other terminal of switch 44 being grounded through circuit board 68 to the ground 82 of the circuit 78. Third, pin P24 of the 8749 microprocessor is connected through the LAMP signal conductor 83 to the 10K ohm resistor in series with the base of the lamp circuit relay switching transistor on circuit board 68 (FIG. 4). Fourth, the battery pack is removed and the VB battery connection of circuit 78 is connected by conductor 84 from the power 3.8 volt supply 77 positive terminal on circuit board 68 (FIG. 4). Fifth, the 8749 microprocessor is reprogrammed in accordance with the assembly listing filed concurrently herewith and expressly incorporated herein in the accompanying software Appendix.

The operating program of circuit 78 generates an output signal to trigger camera 42 and lamp 48 when switch 73 is closed. It does so by generating respective TRIP and LAMP signals to cause the formation of a pictorial image of the person 55 using the tester 50 to be transmitted to the central office 15. The LAMP signal on line 83 persists long enough (e.g., 1 or 2 seconds) to fully illuminate the facial region of person 55 as the image thereof is being formed by camera 42. This ensures that person 55 will be clearly visible and thus, identifiable in the resulting image irrespective of the ambient light level.

Once the pressure switch 73 has remained closed continuously for the approximately 5 seconds required to ensure a valid, deep lung breath sample, a breath alcohol reading is displayed upon display 57. If at any time during this slightly more than five second interval in the delivery of the breath sample, pressure switch 73 opens to signal that the breath sample has been interrupted, the signal will abort the test and reset the program requiring the user to restart the breath test. The display 57 of the breath tester 50 indicates the abort condition by displaying a suitable visual message such as "ABrt". A predetermined time interval, such as 5.2 seconds, following the initial closing of pressure switch 73, a second trip signal is generated under program control on line 81 causing a second image of the person using the tester 50 and display 57 to be formed and transmitted to the central office 15 via telephone exchange 14. That portion of the transmitted image which includes display 57 will show either the abort message or a numerical value indicating the result of the alcohol test. When this image is formed, however, a LAMP signal is preferably not generated on line 83. This helps to ensure that the indicia being shown on display 57 will not be "washed out" and will be clearly visible in the resulting image. The second pictorial image transmitted to the central office 15 may be recorded there on VCR 30 in the same manner as the first picture transmission described above and/or interpreted immediately upon receipt.

Due to the cycle time of the Visitel camera 42 of the preferred embodiment, about five seconds must lapse between consecutive images. To allow for the first image to be transmitted to the central office 15 and to avoid recording background information, the second image must be taken after the first transmission but before the user moves from the tester 50. Thus, the first picture should be triggered sufficiently early in the sample delivery period to insure that the picture will be transmitted in time for the second to be taken before the user moves his head from the tester mouthpiece. This should be at least about five seconds before the test is complete depending on the maximum rate at which camera 42 can form consecutive images. In the preferred embodiment, the first image is triggered shortly and almost immediately after the pressure switch 73 first closes and the second is programmed to be triggered about 5.2 seconds thereafter. Of course, if a camera having a more rapid image repetition rate (shorter cycle time) is employed, timing can be varied to provide even a greater number of images during the time a breath sample is being delivered.

Instead of using display 57 as means to indicate the result of a test, display 57 can optionally be bypassed or supplemented by forming an electrical output signal representing the test result. This signal, which can be either analog or digital in nature, can be transmitted via a suitable communications link from the tester 50, directly to central office 15. There, it can be recorded by means such as VCR 30 and/or immediately evaluated manually or by the computer or other circuitry at the central office 15 to trigger an alarm or otherwise signal that the test has been failed.

The detailed operation of the control circuitry 68 at the remote location 40 is preferably performed by a microprocessor such as an Intel 8749 programmed as set forth in the attached software Appendix, the details of which will be readily understood by those skilled in the art. The operation of this software will now be summarized with reference to the flow charts of FIGS. 6A-6D.

Figure 6A:
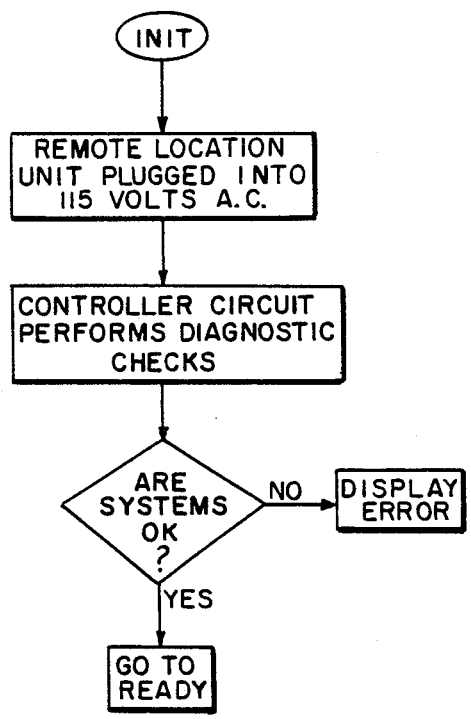
FIGS. 6A-D are flow charts illustrating the operation of the monitoring station of the system under the program control of the microprocessor of the circuit shown in FIG. 5.

Referring first to FIG. 6A, an initial operating procedure, arbitrarily designated INIT, is commenced by applying power to the unit 40 by plugging the unit into a standard 115 volt AC line. When power is applied to the unit, camera control circuit 78 initializes and performs a diagnostic check. This occurs usually when the system is set up in the home of the confinee by probation office personnel. If errors are detected in the system by this automated start-up procedure, an appropriate ERROR is displayed on the display 57 of the tester 50. Otherwise, the operation proceeds to the READY routine illustrated in FIG. 6B.

Figure 6C:
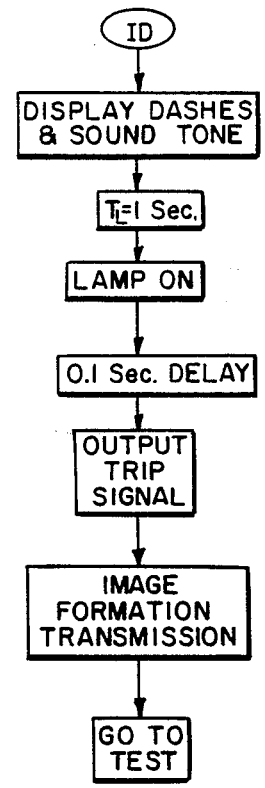
Figure 6B:
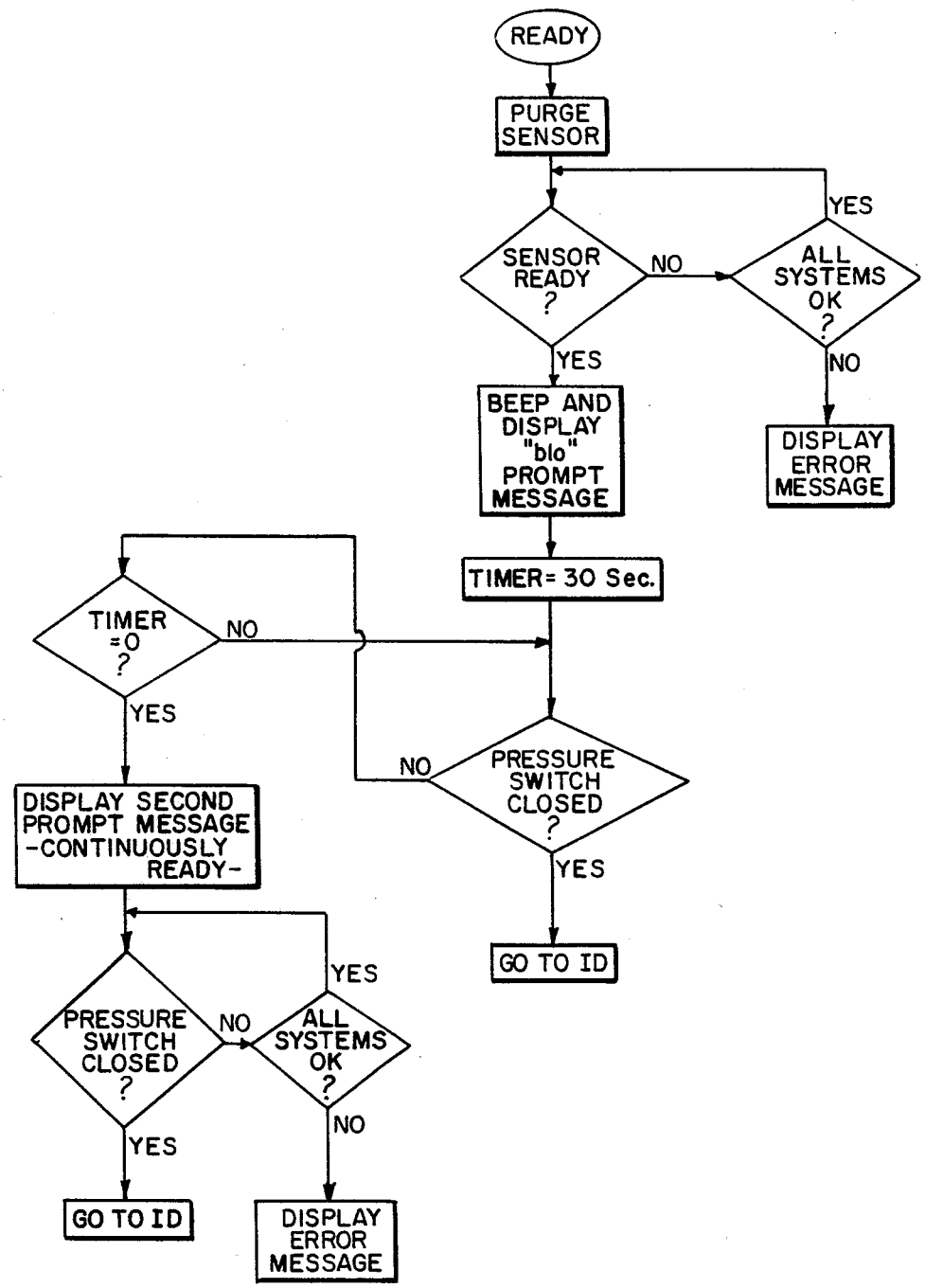

Referring to FIG. 6B, the READY routine commences by energization of a heater associated with the alcohol sensor of tester 50 in a controlled manner to execute the purging of the sensor to prepare it for a test. During this purge routine, additional system checks are made. If an error is detected, display 57 is set to so indicate. The system check occurs during the the sensor purging cycle. During this cycle, the circuitry determines in the manner of the conventional J-4 procedure whether the sensor has been purged. If not, the system diagnostics are repeated and the system loops to continue energizing the sensor heater to purge the sensor. If the sensor purge is complete, the system sounds an audible "beep" and displays a prompting message such as "blo" on display 57 indicating the unit is ready to receive a breath sample. The program then proceeds to set a timer to, for example, 30 seconds, a period within which the user would be required to initiate a breath test at the tester 50. Within this 30 seconds, the program monitors the state of the pressure switch 73 (FIG. 5). If the closure of pressure switch 73 is not sensed within the prescribed time, the program causes a second prompt message to appear and loops through a diagnostic routine while waiting for pressure switch 73 to close. When the switch 73 contacts are made in response to the delivery of a breath sample, the program transfers control to the ID routine described and illustrated in the flow chart of FIG. 6C.

Referring to FIG. 6C, the ID routine begins with a display of dashes ("----") on the tester display 57 so long as pressure switch 73 remains closed. The display of dashes serves as an indication of the closure of the pressure switch 73 which occurs when at least a predetermined minimum flow of breath is present. The program then proceeds to the setting of a timer to a short period, for example, one second, during which the camera lamp 48 will be illuminated. This is caused by the appearance of a signal at P24 of the microprocessor (FIG. 5) and the LAMP output line 83 of the circuit 78. Provided that the arm extension limit switch 71 is closed, closure of the lamp relay 76 will result closing a circuit through switch section 71b to illuminate lamp 48 by applying A.C. voltage to it.

Figure 6D:
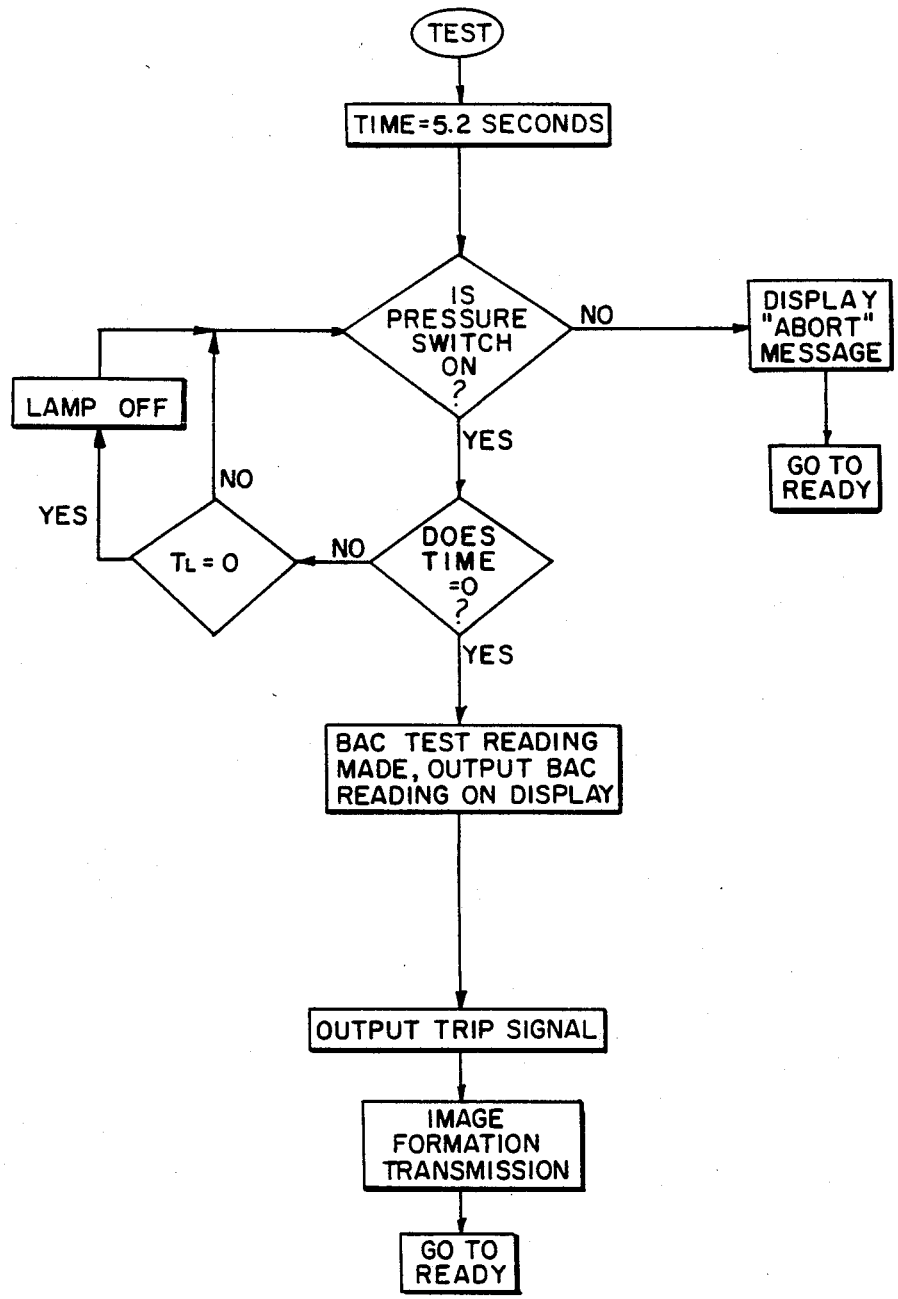

Following illumination of the lamp 48, after a very brief delay of, for example, 1/10th of one second, the controller 78 actuates camera 42 by outputting a trip signal on line 81 from the P23 terminal of the microprocessor (FIG. 5). The short delay allows lamp 48 to warm up enough to assume a sufficient brightness for illumination purposes prior to the formation of an image. The trip signal traverses pole section 71a of limit switch 71 and jumper wires 67. Provided lens cover 47 is open (as indicated by the closure of limit switch 72), camera 42 then forms an image and proceeds to transmit it onto the telephone line 12, through execution of its normal image forming and transmission sequence under control of the circuitry 66. The image will be formed within the time period during which the lamp 48 is on, namely, the one second previously defined. Camera 42 then proceeds to transmit the image serially onto the transmission line according to its normal operating sequence. The program then transfers control to the TEST routine as illustrated in FIG. 6D.

The TEST routine begins with the setting of a timer to 5.2 seconds. This time is longer than the time required to allow the camera 42 to finish transmission of the first image and allows for the timing of a full interval of 5.2 seconds during which a continuous delivery of the breath sample will be required. During this 5.2 seconds, the program repeatedly interrogates the lamp timer to turn lamp 48 off once the timer times out. Also, the program repeatedly tests the output of the pressure switch 73 to determine that the pressure switch 73 (together with the lens cover switch 72 and arm switch 71) is activated indicating that a continuous, uninterrupted breath sample is being delivered. In the event that the circuit is broken by the opening of the pressure switch 73, the test will be aborted, an abort message will appear on display 57 and the system will return to the READY routine of FIG. 6B. If the switch 73 remains closed during the full 5.2 time period thus indicating a valid deep lung breath sample has been delivered, the control circuitry 78 in the breath tester will activate the sensor related circuitry to cause any breath alcohol content reading to be made and the output to be displayed on the display 57 of the tester 50. The controller 78 then generates another TRIP signal to reactivate circuitry of the telecommunications camera 42 to causing it to form a second image and then initiate its transmission to the central office 15. The unit at 40 thereupon remains under the control of the READY routine awaiting the next breath test to be performed in response to the next request from the central office 15.

Having described the programming and operation of controller circuit 78 of the monitoring station at the remote location 40, the overall operation of the system 10 may be described under the control of the program of th computer 20 at the central office 15. This is described with reference to the diagram of FIG. 7.

Figure 7:
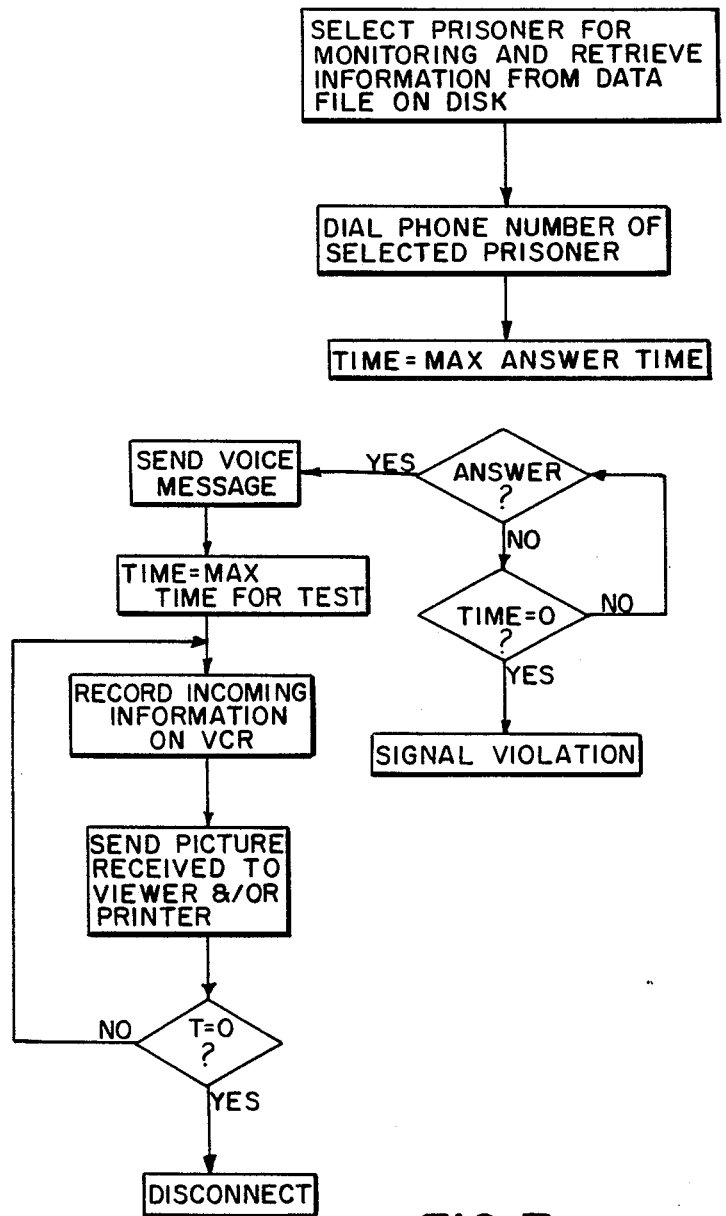
FIG. 7 is a diagram illustrating the operation of the computer at the central office.

Referring to FIG. 7, computer 20 commences operation by initiating the monitoring of a remote location 11 at the central office 15 by the computer 20, which generates a preprogrammed or semi-random command in the central processor 61. Next, computer 20 retrieves from the data storage medium 62 the information necessary to select a specified confinee for monitoring and to establish a communications link with a selected confinee. The computer 20 then initiates the operation of the automatic dialer 63 to dial the phone number of the telephone line to the equipment at the remote location 40 to establish a telephone communications link through the exchange 14 to the remote location 40 at which the selected confinee is assigned. If desired, a maximum response time may be set within which the unit at location 40 must respond, or a signal will indicate an error condition or possible violation. A predetermined number of repeated attempts to establish communication can be programmed before such an error or violation is signalled. When the telephone associated with telecommunications camera 42 with which the remote location 40 is equipped is answered, thereby establishing a connection to the phone line 12, the computer 61 transmits an audible message from the voice synthesizer 64 to the telephone at remote location 40. This message instructs a person at the remote location 40 to respond by performing a breath alcohol test using tester 50. The system then pauses to allow for execution of the program of the remote unit 40 as described above in connection with FIGS. 6A-6D. While the system may be programmed to check incoming information, it is sufficient for it to merely record all incoming information on VCR 30 and to display the images on viewer 33 if manual monitoring is utilized. The program will then disconnect the phone connection.

At the central office 15, the monitoring of a selected confinee to the extent described above has been achieved thus far in fully automated fashion from the central office 15. At this point in the operation, the results, however, will not yet have been analyzed for purposes of identifying the person performing the test at the selected remote location 40 as being the same person as the selected confinee. This may be done manually either at a subsequent time or in real time by viewing the pictorial image received through line 16 over a communications path to the VCR 30 at the central office 15. The image received may be displayed on the viewer 33 and may also be printed out on the printer 38 for present or future comparison with a file image 34. The file image 34 is compared with the image from the viewer 33 representing the picture generated from the remote location 40 to establish whether the two match.

While the above description constitutes a preferred embodiment of the preferred invention, it is to be understood that the invention is not limited thereby and that in light of the present disclosure of the invention, various other alternative embodiments will be apparent to persons skilled in the art. In the first instance, it should be clear that all embodiments of the invention do not require either the step of or means for performing an alcohol test. While particularly well adapted for systems wherein breath alcohol testing is called for, the breath flow responsive monitoring equipment and techniques of the invention are of great utility even in the absence of alcohol testing. It should further be noted that while the preferred embodiment described above utilizes a telecommunications camera that takes still images, the invention could be adapted to video imaging. Also, while the present invention prevents transducing of the transmitted images to a readable form at the central office by requiring a person to blow breath into the monitoring station in order to initiate the forming and transmission of an image, breath flow responsive actuating means could be employed in other ways within the scope of the invention to prevent viewing of the remote confinement location except as authorized by the confinee.

For example, a system could be constructed wherein the central office was unable to transduce a transmitted image in the absence of a code generated as a consequence of using the breath flow responsive actuating means, even if non-transducible images were transmitted periodically or even continuously from the remote location to the central office. Such a code could comprise one or more digital bits transmitted with or separately from image data as an indication that a proper breath signal had been given. Alternatively, images could be periodically or continuously formed by the monitoring station but no image would be transmitted therefrom unless it was one formed at a time the breath flow actuating means was active.

In view of the above, it is clear that various changes can be made without departing from the scope of the invention as particularly pointed out and distinctly claimed in the appended claims.

SOFTWARE APPENDIX

```
J4 Breath Tester
Abort and Power          Service routines

2500 A.D. 8748 Macro Assembler  -  Version 4.02a
------------------------------------------------

Input  Filename : j4.src
            Output Filename : j4.obj

492                                 .list on
493
494                    .extern      ADINT.TEST_PROGRAM.BEEPSR.MEASS.R45R67.SUB16.ONESEC.DISPLY
495                    .extern      ADTOT.HTRADJ.DIV16.MUL16.SAV45.ADCALC.ERRPT.HTRADF.ADD16.BINSEG
496                    .extern      TICK.MEASSF.SUB16R
497                    .page
```

J4 Breath Tester
Main Program Loop

```
498                         **   *** Location Zero:
499                         A
500   03F5                                 .relative
501   0000                                 .org       0
502   0000   04 00                         JMP        INIT
503
504                         ;***** Hardware Interrupt Vector
505   0002
506   0003                                 .org       3
507   0003   04 00                         JMP        ADINT
508                            .page
509                         **   *** INIT:    Power up initialization and charger insertion routine
509
510   0005
511   0060                                 .CODE
512   0000                                 .org       0000
513
514   0000   27              INIT:         CLR        A
515   0001   D7                            MOV        PSW,A
516   0002   35                            DIS        TCNTI
517   0003   15                            DIS        I
518   0004   23 F0                         MOV        A,#(INPUTS!LAMP)
519   0006   3A                            OUTL       P2,A            ;Initialize ports
520   0007   23 E0                         MOV        A,#DBINIT
521   0009   02                            OUTL       BUS,A
522   000A
523   000A   B8 1E                         MOV        R0,#BANK1       ;Clear Ram
524   000C   B0 00           CLEAR:        MOV        @R0,#0
525   000E   18                            INC        R0
526   000F   F8                            MOV        A,R0
527   0010   03 9F                         ADD        A,#-(ENDRAM+1)
528   0012   96 0C                         JNZ        CLEAR
529   0014                                 set        CAL.00
533   0018   D5                            SEL        RB1
534   0019   BB 01                         MOV        DIGIT,#01H      ;First Int . decrements timer
535
536   001B   BC FF                         MOV        INT30,#0FFH     ;3.2ms interrupt rate
537   001D   23 00                         MOV        A,#TICK         ;Load interrupt counter value
538   001F   62                            MOV        T,A
539   0020   55                            STRT       T
540   0021   25                            EN         TCNTI           ;Enable timer interrupts
541
542   0022   C5                            SEL        RB0
543                            .page
544                         **   *** TEST_REQ:   Test program requested by grounding PORT A
545   0023
546   0023
547   0023   0A              TEST_REQ:     IN         A,P2            ;Test routine requested ???
548   0024   53 40                         ANL        A,#REED
549   0026   96 2A                         JNZ        TR1
550   0028   46 2A                         JNT1       TR1
551                                        CALL       TEST_PROGRAM    ;Yes - perform test program
552                                        ;                          routine never returns
553
554   002A                   TR1:
555
556
557                            .page
558                         **   *** MAIN:    Main program Loop
559                         A
560   002A
561   002A
562                            .page
563   002A
564   002A                   START_UP:     relay_on
567   002C   14 00                         CALL       BEEPSR          ;"BEEP"
568   002E                                 display    SEGTST          ;All segments on
572   0032                                 timer      1,1
578   0039   18                            INC        R0
579
580   003A   F0              SU1:          MOV        A,@R0
581   003B   96 3A                         JNZ        SU1
582   003D
583   003D   14 00                         CALL       MEASS           ;Measure sensor channel
584   003F   14 00                         CALL       R45R67          ;Move to R6,R7
585   0041   BA 0A                         MOV        R2,#<10         ;Subtract 10
586   0043   BB 00                         MOV        R3,#>10
587   0045   14 00                         CALL       SUB16           ;SENSOR > 10 ???
588   0047   FB                            MOV        A,R3
589   0048   B8 52                         MOV        R0,#BLT10
590   004A   37                            CPL        A
591   004B   F2 4F                         JB7        PURGE_ON
592   004D   B0 FF           START_1:      MOV        @R0,#0FFH       ;Yes - BLT10 SET
593
594                            .page
                                subtitle
595                         ;***** PURGE:       Sensor Purge
596
597
598                         ;              1    Unit must be ready at or before 90 sec.
599                         ;              2    If peak exists, the unit must be on 75 seconds before
600                         ;                   monitoring the baseline
601                         ;              3    After any ABORTs do not look for peak
602                         ;              4    If peak not found monitor baseline after 25 secs
603                         ;
604                         ;       Case   A    5sec low heat
605                         ;              B    No special start
```

```
606                            ;          C      5 sec BLAST - standard
607                            ;          D      10 sec BLAST, power down at 140 sec
608                            ;          E      15 sec BLAST, power down at 140 sec
609   004F
610   004F               PURGE_ON:    display  ONPAT              :"ON"
614
615   0053               PURGE:       set      RTIMER.0           :Reset READY timer
619   0057                            set      TUP.25             :Reset TUP
623   005B                            set      BLAST.5            :5 sec BLAST
627   005F
628   005F  14 00        PURGE1:      CALL     ONESEC             :Timer = 1 sec
629   0061                            get      ABCNT              :ABORT ???
633   0064  C6 68                     JC       PEAK?              :No - Look for peak
634   0066  04 90                     JMP      REGULATE_HEAT      :Yes - No PEAK ,HEATER = startup level
635                                 .page J4 Breath Tester
        Sensor Purge 636                            ;  ;* PEAK?        Look for Peaking purge
637
638   0068  14 00        PEAK?        CALL     MEASS              :Measure SENSOR
639   006A  14 00                     CALL     R45R67
640
641   006C  BA AA                     MOV      R2,#<170           :SENSOR < 170 ???
642   006E  BB 00                     MOV      R3,#>170
643   0070  14 00                     CALL     SUB16
644   0072  FB                        MOV      A,R3
645   0073  F2 7E                     JB7      BLAST?             :No  - bypass ***** DOUBLE CHECK
646
647   0075                            get      BLT10              :Yes - if bias >10 extend purge
651   0078  C6 7E                     JC       BLAST?
652   007A
653   007A               PEAK_FOUND:  set      TUP.75             :TUP=75, Extend PURGE
657                                 .page
658                            ;** ;*** BLAST?
659   007E               BLAST?:      get      BLAST              :RTIMER < BLAST ???
663   0081  37                        CPL      A
664   0082  17                        INC      A
665   0083  B8 28                     MOV      R0,#RTIMER
666   0085  60                        ADD      A,@R0
667   0086  37                        CPL      A
668   0087  F2 90                     JB7      REGULATE_HEAT      :No - HEATER at startup BLAST
669
670   0089  B9 4D        HIGH_HEAT:   MOV      R1,#HEATER         :No - HEATER at high heat
671   008B  B1 13                     MOV      @R1,#19
672   008D  19                        INC      R1
673   008E  B1 00                     MOV      @R1,#0
674
675   0090  14 00        REGULATE_HEAT: CALL   HTRADJ
676   0092  B8 28                     MOV      R0,#RTIMER         :RTIMER > TUP ???
677   0094  F0                        MOV      A,@R0
678   0095  37                        CPL      A
679   0096  17                        INC      A
680   0097  B8 51                     MOV      R0,#TUP
681   0099  60                        ADD      A,@R0
682   009A  F2 B5                     JB7      BASELINE           :Yes - find the baseline
683                                 .page
684                            ;*** ;** VOLTAGE_TEST:  Check for charger
685                            ;***** PS_TEST:         Test for closed pressure switch
686
687
688
689   009C  36 A2        VOLTAGE_TEST: JT0     PS_TEST             :BATTERY TEST
690   009E                            error    1
694
695   00A2  0A           PS_TEST:     IN       A,P2
696   00A3  53 80                     ANL      A,#PSMSK
697   00A5  96 AB                     JNZ      PURGE_SCAN
698   00A7                            error    3
702
703
704
705                            ;***** PURGE_SCAN: Scan through purge cycle one every second
706                            ;                  Wait here until current second is over
707                            ;                  Then decrement RTIMER
708                            ;
709
710   00AB               PURGE_SCAN   get      TFPAC
714   00AE  96 9C                     JNZ      VOLTAGE_TEST       :Second up ???   No - wait for it
715   00B0  B8 28                     MOV      R0,#RTIMER
716   00B2  10                        INC      @R0
717   00B3  04 5F                     JMP      PURGE1             :Yes - scan through purge cycle
718
719
720                                 .page J4 Breath Tester
        Find stable baseline
                                      Subtitle
721                            ;     title Find stable baseline
722                            ;***** BASELINE:     Find the BASELINE
723                            ;
724   00B5               BASELINE:    set      READY.0            :Clear READY timer
728   00B9  BC FF                     MOV      R4,#-1             :Clear the sample buffer
729   00BB
730   00BB  1C           INIT_BUFFER: INC      R4                 :Initialize sample buffer
```

```
731  00BC  FC                              MOV    A,R4
732  00BD  03 F9                           ADD    A,#-NUMSAM      ;All of buffer initialized
733  00BF  C6 CD                           JZ     SAMPLE_PTR      ;Yes -
734
735  00C1  23 35                           MOV    A,#READ         ;No - form address of next element
736  00C3  6C                              ADD    A,R4
737  00C4  6C                              ADD    A,R4            ;(word data)
738  00C5  A8                              MOV    R0,A
739
740  00C6  B0 26                           MOV    @R0,#>50        ;Sample = 550 ,arbitraily high
741  00C8  18                              INC    R0
742  00C9  B0 02                           MOV    @R0,#>550
743  00CB  04 BB                           JMP    INIT_BUFFER     ;Continue to initialize all of buufer
744                          .page
745
746                          ;***** SAMPLE:        Sample baseline looking for steady values
747
748  00CD              SAMPLE_PTR:   set    SP,00                 ;Initialize sample pointer
752
753  00D1  14 00       BASE_SAMPLE:  CALL   ONESEC                ;TIMER=1SEC
754  00D3                            get    READY                 ;READY = 0 ???
758  00D6  C6 DA                     JZ     CHECK_90              ;Yes - don't BEEP
759  00D8  14 00                     CALL   BEEPSR                ;No  - BEEP
760  00DA
761  00DA  B8 28       CHECK_90:     MOV    R0,#RTIMER            ;90 seconds max from HIGH HEAT
762  00DC  10                        INC    @R0
763  00DD  F0                        MOV    A,@R0
764  00DE  03 A6                     ADD    A,#-90                ;90 seconds over ???
765  00E0  96 E4                     JNZ    SAMPLE
766  00E2  24 7F                     JMP    SENSOR_READY          ;Yes - default READY
767
768  00E4  14 00       SAMPLE:       CALL   HTRADF                ;Fast HEATER adjustment
769  00E6  14 00                     CALL   MEASSF                ;Read SENSOR
770  00E8  B9 2F                     MOV    R0,#SNOW              ;Save at SAMPLE pointer
771  00EA  14 00                     CALL   SAV45
772
773  00EC                            get    READY                 ;READY ???
777  00EF  C6 F3                     JZ     STORE_SAMPLE          ;
778  00F1  24 69                     JMP    CHECK_READY
779
780                          .page
781                          ;***** STORE_SAMPLE       Store the current sample in the buffer
782                          ;
783                          ;     Input:   R0       Points to sample counter
784
785  00F3         STORE_SAMPLE:     get    SP                    ;Form buffer offset
788  00F6  E7                       RL     A                     ;(Word data)
789  00F7  B8 35                    MOV    R0,#READ              ;Top of buffer
790  00F9  68                       ADD    A,R0                  ;Form sample address
791  00FA
792  00FA  A8                       MOV    R0,A                  ;Store current sample LB
793  00FB  B9 2F                    MOV    R1,#SNOW
794  00FD  F1                       MOV    A,@R1
795  00FE  A0                       MOV    @R0,A
796
797  00FF  18                       INC    R0                    ;Store current sample HB
798  0100  19                       INC    R1
799  0101  F1                       MOV    A,@R1
800  0102  A0                       MOV    @R0,A
801
802  0103  B8 2C                    MOV    R0,#SP                ;Sample pointer at end of buffer ???
803  0105  10                       INC    @R0
804  0106  F0                       MOV    A,@R0
805  0107  03 F9                    ADD    A,#-NUMSAM
806  0109  96 0D                    JNZ    INIT_MAXMIN
807  010B  B0 00                    MOV    @R0,#00               ;Yes - reset
808
809
810                          ;***** INIT_MAXMIN:      Initialize Max, Min values
811
812  010D  B8 31       INIT_MAXMIN:  MOV    R0,#RMAX              ;RMAX=0
813  010F  B0 00                     MOV    @R0,#0
814  0111  18                        INC    R0
815  0112  B0 00                     MOV    @R0,#0
816
817  0114  B8 33                     MOV    R0,#RMIN              ;RMIN=#8000H  (largest -ve value)
818  0116  B0 00                     MOV    @R0,#0
819  0118  18                        INC    R0
820  0119  B0 80                     MOV    @R0,#80H
821
822  011B  BC FF                     MOV    R4,#-1                ;Sample counter in R4
823  011D  1C          NEXT_SAMPLE:  INC    R4
824  011E  FC                        MOV    A,R4
825  011F  03 F9                     ADD    A,#-(NUMSAM)          ;All samples checked for max.min
826  0121  C6 60                     JZ     CHK_RANGE             ;Yes - check range
827
828  0123  23 35                     MOV    A,#READ               ;No - point to next sample
829  0125  6C                        ADD    A,R4
830  0126  6C                        ADD    A,R4
831  0127  A8                        MOV    R0,A
832  0128
833                          .page
834                          ;***** MAX:        Check if SAMPLE is larger then MAX
835                                           If yes then new MAX = SAMPLE
836
837  0128  F0          MAX:          MOV    A,@R0                 ;Get SAMPLE
838  0129  AE                        MOV    R6,A
839  012A  18                        INC    R0
840  012B  F0                        MOV    A,@R0
841  012C  AF                        MOV    R7,A
```

```
842  012D  C8                             DEC     R0
843
844  012E  B9 31                  MOV     R1,#RMAX        ;RMAX in R2,R3
845  0130  F1                     MOV     A,@R1
846  0131  AA                     MOV     R2,A
847  0132  19                     INC     R1
848  0133  F1                     MOV     A,@R1
849  0134  AB                     MOV     R3,A
850  0135  C9                     DEC     R1
851
852  0136  14 00                  CALL    SUB16           ;MAX > SAMPLE ???
853  0138  FB                     MOV     A,R3
854  0139  F2 43                  JB7     MIN             ;Yes - check for minimum
855  013B
856  013B  F0                     MOV     A,@R0           ;MAX = SAMPLE
857  013C  A1                     MOV     @R1,A
858  013D  18                     INC     R0
859  013E  19                     INC     R1
860  013F  F0                     MOV     A,@R0
861  0140  A1                     MOV     @R1,A
862  0141  C8                     DEC     R0
863  0142  C9                     DEC     R1
864
865                        .page
866                ;**  **  MIN:   IF SAMPLE < MIN then new MIN=SAMPLE
867                ;
868
869  0143  F0             MIN:    MOV     A,@R0           ;Get SAMPLE
870  0144  AA                     MOV     R2,A
871  0145  18                     INC     R0
872  0146  F0                     MOV     A,@R0
873  0147  AB                     MOV     R3,A
874  0148  C8                     DEC     R0
875  0149
876  0149  B9 33                  MOV     R1,#PMIN        ;Get MIN
877  014B  F1                     MOV     A,@R1
878  014C  AE                     MOV     R6,A
879  014D  19                     INC     R1
880  014E  F1                     MOV     A,@R1
881  014F  AF                     MOV     R7,A
882  0150  C9                     DEC     R1
883  0151
884  0151  14 00                  CALL    SUB16           ;SAMPLE > MIN ???
885  0153  FB                     MOV     A,R3
886  0154  F2 1D                  JB7     NEXT_SAMPLE     ;Yes - test next SAMPLE
887
888  0156  F0                     MOV     A,@R0           ;MIN = SAMPLE
889  0157  A1                     MOV     @R1,A
890  0158  18                     INC     R0
891  0159  19                     INC     R1
892  015A  F0                     MOV     A,@R0
893  015B  A1                     MOV     @R1,A
894  015C  C8                     DEC     R0
895  015D  C9                     DEC     R1
896  015E
897  015E  24 1D                  JMP     NEXT_SAMPLE
898                        .page
899                ;**  ** CHK_RANGE:      Check that MAX - MIN SAMPLE readings are within
900                ;                      RANGE of each other. ei stable baseline
901
902  0160
903  0160  B8 31          CHK_RANGE:  MOV R0,#RMAX        ;RMAX in R6,R7
904  0162  F0                     MOV     A,@R0
905  0163  AE                     MOV     R6,A
906  0164  18                     INC     R0
907  0165  F0                     MOV     A,@R0
908  0166  AF                     MOV     R7,A
909
910  0167  B8 33                  MOV     R0,#RMIN        ;RMIN in R2,R3
911  0169  F0                     MOV     A,@R0
912  016A  AA                     MOV     R2,A
913  016B  18                     INC     R0
914  016C  F0                     MOV     A,@R0
915  016D  AB                     MOV     R3,A
916
917  016E  14 00                  CALL    SUB16           ;RMAX - RMIN
918  0170  FA                     MOV     A,R2
919  0171  AE                     MOV     R6,A
920  0172  FB                     MOV     A,R3
921  0173  AF                     MOV     R7,A            ;Save in R6,R7
922
923  0174  BA 02                  MOV     R2,#>RANGE
924  0176  BB 00                  MOV     R3,#<RANGE
925  0178  14 00                  CALL    SUB16           ;(RMAX - RMIN) - RANGE < 0 ???
926  017A  FB                     MOV     A,R3
927  017B  F2 7F                  JB7     SENSOR_READY    ;Yes - Unit ready for test
928  017D  24 89                  JMP     CHECK_READY
929                        .page
930                ;**  ** SENSOR_READY:   Sensor ready for test
931                ;
932                ;               Conditions:     1       Stable baseline
933                ;                               2       90 sec max purge
934
935                ;               Description:    Increment READY which counts the # of seconds ready
936                ;                                       If ready longer then 27 seconds power down
937                ;                                       Wait for current sec to finish then monitor baseline
938                ;                                       If blowing then go to blowing routine
939
940  017F           SENSOR_READY:  display BLIPAT          ;Display "blo"
```

```
944   0183                                        set      READY,1            ;Set unit as ready
948   0187
949   0187   14 00                                CALL     BEEPSR             ;BEEP
950
951   0189                   CHECK_READY:         get      READY              ;Check if sensor is ready
955   018C   C6 AA                                JZ       NOT_READY
956   018E
957   018E   B8 27           RDY:                 MOV      R0,#READY          ;Yes - READY=READY+1
958   0190   10                                   INC      @R0
959   0191
960   0191   F0                                   MOV      A,@R0              ;READY · 27 sec ???
961   0192   03 E5                                ADD      A,#-27
962   0194   96 98                                JNZ      RDY0
963   0196   64 19                                JMP      OFF                ;Yes - Power down
964
965   0198   B8 20           RDY0:                MOV      R0,#TFRAC
966   019A   F0              RDY1:                MOV      A,@R0
967   019B   96 9F                                JNZ      RDY2               ;FOREVER
968   019D   04 D1                                JMP      BASE_SAMPLE
969
970   019F   36 A3           RDY2:                JT0      CHECK_BLOW
971   01A1   64 22                                JMP      BATLOW
972
973   01A3   0A              CHECK_BLOW:          IN       A,P2
974   01A4   53 80                                ANL      A,#PSMSK           ;PS = closed ???
975   01A6   C6 BE                                JZ       BLOW               ;Yes - service blow
976   01A8   24 9A                                JMP      RDY1               ;No  -
977
978                          .page
979                          ;***** NOT_READY    If unit is not ready wait for current second to
980                          ;                   be over then continue scanning baseline.
981
982   01AA   B8 20           NOT_READY:           MOV      R0,#TFRAC          ;Current second over ???
983   01AC   F0                                   MOV      A,@R0
984   01AD   96 B1                                JNZ      NRDY1              ;No - check power supply
985   01AF   04 D1                                JMP      BASE_SAMPLE        ;Yes - monitor baseline
986
987   01B1   36 B5           NRDY1:               JT0      NRDY2
988   01B3   64 22                                JMP      BATLOW
989
990   01B5   0A              NRDY2:               IN       A,P2
991   01B6   53 80                                ANL      A,#PSMSK
992   01B8   96 AA                                JNZ      NOT_READY          ;TISK TISK TISK
993   01BA                                        error    3
997                          .page ;4 Breath Tester
      ;Blowing
998                                              .title Blowing
999                          ;***** BLOW         Blowing started
1000                         ;                   Turn of HEATER , constant BEEP
1001                         ;                   Wait for PS to be closed for BLOW_TIME
1002                         ;                   BLOW_TIME = Time to blow sec / 3.2 ms
1003
1004  01BE                   BLOW:                lamp_on
1007  01C0                                        set      HEATER,00          ;Turn HEATER off
1011  01C4                                        display  DASHPT             ;DISPLAY"----"
1015  01C8                                        set      BEEP,0FFH          ;Constant BEEP
1019
1020  01CC                                        timer    0,10               ;Wait for .1 sec for lamp to illuminate
1026  01D3   F0              LAMP_WAIT:           MOV      A,@R0
1027  01D4   96 D3                                JNZ      LAMP_WAIT
1028
1029  01D6                                        set      SEND,150           ;Push SEND button to send PICTURE 1
1033                                              ;                           Button pushed for 150*12.8ms = 1 sec
1034                                              ;                           LAMP turned off by SEND
1035
1036  01DA   B8 1E                                MOV      R0,#PSTLO          ;Pressure switch timer, PSTIMER
1037  01DC   B9 5A                                MOV      R1,#TMP1           ;Length of blow reference
1038  01DE   B1 B7                                MOV      @R1,#<BLOW_TIME
1039  01E0   19                                   INC      R1
1040  01E1   B1 06                                MOV      @R1,#>BLOW_TIME
1041  01E3   C9                                   DEC      R1
1042
1043  01E4   14 00           STILL_BLOWING:       CALL     SUB16R             ;PSTIMER - BLOW_TIME < 0 ???
1044  01E6   F6 EF                                JC       BLOCMP             ;Yes - blow over
1045  01E8
1046  01E8   0A                                   IN       A,P2               ;Pressure switch = closed ???
1047  01E9   53 80                                ANL      A,#PSMSK
1048  01EB   C6 E4                                JZ       STILL_BLOWING      ;Yes - check time
1049  01ED   44 F9                                JMP      ABORT              ;No - aborted test
1050                         .page ;4 Breath Tester
      ;Blow completed. determine BAC 1051                                              .title Blow completed, determine BAC
1052                         ;***** BLOCMP       Blow complete
1053                         ;                   Measure SENSOR
1054
1055
1056  01EF   14 00           BLOCMP:              CALL     MEASS              ;Measure SENSOR
1057  01F1                                        set      SEND,200
1061  01F5                                        set      BEEP,0             ;Turn beeper off
1065  01F9
1066  01F9   B8 2A                                MOV      R0,#SS2            ;Save at SS2
1067  01FB   14 00                                CALL     SAV45
1068  01FD
1069                         .page
```

```
1070                    *** ** CHECK_POT: Check that the USER POT has not been bottomed or topped out
1071                    :
1072   01FD  BA 02      CHECK_POT:   MOV    R2,#CCHAN      ;Measure USER POT
1073   01FF  B9 44                   MOV    R1,#XTOTAL
1074   0201  14 00                   CALL   ADTOT
1075   0203  14 00                   CALL   ADCALC         ;Result in R4,R5
1076   0205  B8 53                   MOV    R0,#SUSER      ;Save at SUSER
1077   0207  14 00                   CALL   SAV45
1078   0209  14 00                   CALL   R45R67         ;Also SUSER in R6,R7
1079
1080
1081   020B  BA 05      LOW_POT:     MOV    R2,#>5         ;R2,R3=5
1082   020D  BB 00                   MOV    R3,#>5
1083   020F  14 00                   CALL   SUB16          ;R2,R3=SUSER-5
1084   0211  FB                      MOV    A,R3
1085   0212  37                      CPL    A              ;SUSER > 5 ???
1086   0213  F2 19                   JB7    HIGH_POT       ;Yes - check high end
1087   0215                          error  4
1091   0219
1092   0219  FA         HIGH_POT:    MOV    A,R2           ;R6,R7=SUSER-5
1093   021A  AE                      MOV    R6,A
1094   021B  FB                      MOV    A,R3
1095   021C  AF                      MOV    R7,A
1096   021D  BA EA                   MOV    R2,#<490
1097   021F  BB 01                   MOV    R3,#>490
1098   0221  14 00                   CALL   SUB16          ;R2,R3=SUSER-5-490
1099   0223  FB                      MOV    A,R3
1100   0224  F2 2A                   JB7    FUDGE          ;SUSER > 495 ???
1101   0226                          error  4              ;Yes -Display error and power down
1105
1106                                .page J4 Breath Tester
                    Analyse Sensor reading
1107                                .title, Analyse Sensor reading
1108                                ;***** FUDGE:   Fudge the sample reading
1109                                ;                SENSOR = SENSOR - 5
1110                                ;               If SENSOR > 10 then  SENSOR = (10-2(10-SENSOR))
1111   022A
1112   022A  B8 2A      FUDGE:       MOV    R0,#S52
1113   022C  F0                      MOV    A,@R0
1114   022D  AE                      MOV    R6,A
1115   022E  18                      INC    R0
1116   022F  F0                      MOV    A,@R0
1117   0230  AF                      MOV    R7,A
1118
1119   0231  BA 05      SUB5:        MOV    R2,#05
1120   0233  BB 00                   MOV    R3,#00
1121   0235  14 00                   CALL   SUB16          ;SENSOR - 5
1122   0237
1123   0237  FB                      MOV    A,R3           ;SENSOR < 5 ???
1124   0238  F2 55                   JB7    MAKE0          ;Yes - zero the reading
1125   023A  96 59                   JNZ    ADJCAL         ;>255
1126   023C
1127   023C  FA                      MOV    A,R2           ;Get SENSOR LB
1128   023D  F2 59                   JB7    ADJCAL         ;
1129   023F  C6 55                   JZ     MAKE0          ;Yes - zero the reading
1130   0241
1131   0241  03 F6                   ADD    A,#-10         ;No - SENSOR > 10 ???
1132   0243  37                      CPL    A
1133   0244  F2 59                   JB7    ADJCAL         ;>9
1134
1135                                ;***** LOW_FUDGE:   Fudge low readings
1136   0246
1137   0246  FA         LOW_FUDGE:   MOV    A,R2           ;No - SENSOR =10 - 2*(10 - SAMPLE
1138   0247  37                      CPL    A
1139   0248  17                      INC    A
1140   0249  03 0A                   ADD    A,#10
1141   024B  E7                      RL     A
1142   024C  37                      CPL    A
1143   024D  17                      INC    A
1144   024E  03 0A                   ADD    A,#10
1145   0250  F2 55                   JB7    MAKE0
1146   0252  AA                      MOV    R2,A
1147   0253  44 59                   JMP    ADJCAL
1148
1149                                ;***** MAKE0:   Force the SENSOR reading to zero
1150
1151   0255  BA 00      MAKE0:       MOV    R2,#0
1152   0257  BB 00                   MOV    R3,#0
1153
1154                                .page
1155                    *****  *** ADJCAL:   Adjust SENSOR reading to reflect USER POT setting
1156                                ;                SENSOR = SENSOR*SUSER/330
1157                                ;               Therefore if SUSER = 0 then Gain = 0.5
1158                                ;                         if SUSER = 500   Gain = 2
1159
1160   0259  FA         ADJCAL:      MOV    A,R2
1161   025A  AC                      MOV    R4,A
1162   025B  FB                      MOV    A,R3
1163   025C  AD                      MOV    R5,A
1164
1165   025D  B8 53                   MOV    R0,#SUSER      ;SUSER IN R6,R7
1166   025F  F0                      MOV    A,@R0
1167   0260  AE                      MOV    R6,A
1168   0261  18                      INC    R0
1169   0262  F0                      MOV    A,@R0
```

```
1170  0263  AF                              MOV    R7,A
1171  0264
1172  0264  B8 A7                           MOV    R0,#167       ;167 IN R0,R1
1173  0266  B9 00                           MOV    R1,#0
1174  0268  14 00                           CALL   ADD16         ;SUSER+167 IN R0,R1
1175  026A  F9                              MOV    A,R1          ;MOVE TO R2,R3
1176  026B  AB                              MOV    R3,A
1177  026C  F8                              MOV    A,R0
1178  026D  AA                              MOV    R2,A
1179  026E
1180  026E  14 00                           CALL   MUL16         ;RESULT IN R2 TO R5
1181  0270
1182  0270  FD                              MOV    A,R5          ;MOVE IT TO R4 - R7
1183  0271  AF                              MOV    R7,A
1184  0272  FC                              MOV    A,R4
1185  0273  AE                              MOV    R6,A
1186  0274  FB                              MOV    A,R3
1187  0275  AD                              MOV    R5,A
1188  0276  FA                              MOV    A,R2
1189  0277  AC                              MOV    R4,A
1190  0278
1191  0278  BA 4D                           MOV    R2,#<333      ;333 IN R2,R3
1192  027A  BB 01                           MOV    R3,#>333
1193  027C  14 00                           CALL   DIV16
1194                        .page
1195                  ;*** CHECK_PWF         Check if unit is to display as PWF
1196                  ;
1197                  ;       Option byte:   D2 or D3 =1    PWF
1198                  ;                      D2 and D3  =0  Digital
1199  027E
1200  027E             CHECK_PWF:    cjnz    CAL_DIGITAL   ;Calibrate mode ???
1205
1206  0283                           get     OPTION        ;Test OPTIONS 1= PWF, 1= DIGITAL
1210  0286  52 91                    JB2     PWFVER        ;Test BIT 2
1211  0288  72 91                    JB3     PWFVER        ;If diode 3 then check FAIL level
1212
1213
1214
1215
1216                  ;***** DIGITAL         Digital version - display SENSOR reading
1217
1218  028A  FD        DIGITAL:       MOV     A,R5          ;Display SENSOR reading digitally
1219  028B  AA                       MOV     R2,A
1220  028C  FC                       MOV     A,R4
1221  028D  14 00                    CALL    BINSEG
1222  028F  44 BC                    JMP     WT13          ;Wait 1/4 sec
1223                  .page
1224                  ;*** PWFVER:           Pass. Warn. Fail display
1225  0291
1226        0064      FAIL    EQU    100
1227        0032      WARN    EQU    50
1228  0291
1229  0291  FD        PWFVER:        MOV     A,R5          ;Result into R2,R3
1230  0292  AB                       MOV     R3,A
1231  0293  FC                       MOV     A,R4
1232  0294  AA                       MOV     R2,A
1233
1234  0295  BE 63     FAIL?:         MOV     R6,#<FAIL-1   ;SENSOR > FAIL ???
1235  0297  BF 00                    MOV     R7,#>FAIL-1
1236  0299  14 00                    CALL    SUB16
1237  029B  FB                       MOV     A,R3
1238  029C  F2 B8                    JB7     FAILEX        ;Yes - Display fail message
1239
1240  029E             CHECK_DIGIFAIL: get    OPTION        ;If DIGI-FAIL then display DIGITAL
1244  02A1  72 8A                    JB3     DIGITAL
1245  02A3
1246  02A3  FD        WARN?:         MOV     A,R5          ;SENSOR > WARN ???
1247  02A4  AB                       MOV     R3,A
1248  02A5  FC                       MOV     A,R4
1249  02A6  AA                       MOV     R2,A
1250  02A7  BE 31                    MOV     R6,#<WARN-1
1251  02A9  BF 00                    MOV     R7,#>WARN-1
1252  02AB  14 00                    CALL    SUB16         ;Yes - Display Warn message
1253  02AD  FB                       MOV     A,R3
1254  02AE  F2 B4                    JB7     WARNEX
1255                  .page
1256                  ;*** DISPLAY PASS,WARN,FAIL and wait
1257
1258  02B0             PASSEX:        load_display PASSPT
1261  02B2  44 BA                    JMP     PWFDIS
1262
1265  02B4             WARNEX:        load_display WARNPT
1266  02B6  44 BA                    JMP     PWFDIS
1267
1269  02B8             FAILEX:        load_display FAILPT
1270  02BA  14 00      PWFDIS:        CALL    DISPLY
1272
1273  02BC             WT13:          cjz     CAL_DISPLAY_RESULT ;Cal mode ???
1278  02C1  24 FD                    JMP     CHECK_POT     ;Out of page jump
1279                  .page
1280
1281                  ;***** DISPLAY_RESULT: Display result for 25 sec beeping at 5 and 10 sec
1282                  ;                     before powering down
1283  02C3
1284
1285  02C3             DISPLAY_RESULT: set    HEATER,HTR_PURGE ;Purge Sensor
1289  02C7  18                       INC     R0
1290  02C8  B0 01                    MOV     @R0,#01
1291
```

```
1292  02CA                            timer      disp.
1298  02D1    19                      INC        R0                  ;Point at TSEC
1299
1300
1301  02D2    1A      DISPLAY_ON:     IN         A,P2                ;REEDSWITCH = closed ???
1302  02D3    53 40                   ANL        A,#REED
1303  02D5    96 DD                   JNZ        DR2
1304  02D7            set CAL,45                                     ;Yes - Set Cal mode timer
1308  02D9    24 FD                   JMP        CHECK_POT           ;     Recaiculate display value
1309
1310                  DR2::           MOV        R1,#TSEC            ;Delay before sending picture
1311                      :           MOV        A,@R1
1312                      :           XRL        A,disp-3
1313                      :           JNZ        DR22
1314                      :           set SEND,50
1315
1316  02DD    B9 20   DR22:           MOV        R1,#TFRAC           ;TIMER = 0 ????
1317  02DF    F1                      MOV        A,@R1
1318  02E0    96 E4                   JNZ        DR25
1319  02E2    64 19                   JMP        OFF                 ;Exit when time up
1320
1321  02E4    07      DR25:           DEC        A
1322  02E5    96 D2                   JNZ        DISPLAY_ON          ;JUMP BACK IF TFRAC
1323  02E7    F0                      MOV        A,@R0
1324  02E8    03 FB                   ADD        A,#-5               ;BEEP IF 5 SEC LEFT
1325  02EA    C6 F0                   JZ         DR3
1326  02EC    03 FB                   ADD        A,#-5               ;BEEP IF 10 SEC LEFT
1327  02EE    96 D2                   JNZ        DISPLAY_ON
1328
1329  02F0    F8      DR3:            MOV        A,R0                ;SAVE R0
1330  02F1    AB                      MOV        R3,A
1331  02F2    14 30                   CALL       BEEPSR
1332  02F4    FB                      MOV        A,R3                ;RETURN R0
1333  02F5    A8                      MOV        R0,A
1334  02F6    44 D2                   JMP        DISPLAY_ON
1335
1336                  .page
```

;4 Breath Tester
Abort and Power service routines

```
1337                  ;       Abort and Power service routines
1338                  ;***** ABORT:           Abort service
1339
1340                  :       Called:  1       Blow pressure at an illegal time
1341                  :                2       Blow pressure not maintained during test
1342  02F8
1343
1344  02F8            ABORT:          set        BEEP,00             ;Turn BEEP off
1348  02FC                            set        HEATER,00           ;Turn HEATER off
1352  0300                            display    ABTPAT              ;Display abort message
1356
1357  0304    14 00                   CALL       ONESEC              ;Wait one second
1358  0306    F0      AB1:            MOV        A,@R0
1359  0307    96 06                   JNZ        AB1
1360
1361  0309    14 30                   CALL       BEEPSR              ;BEEP
1362  030B    B8 29                   MOV        R0,#ABCNT           ;Increment ABORT counter
1363  030D    10                      INC        @R0
1364  030E    F0                      MOV        A,@R0
1365  030F    03 FD                   ADD        A,#-3               ;Third ABORT   ???
1366  0311    C6 15                   JZ         ABORT_ERROR
1367  0313    04 53                   JMP        PURGE
1368  0315            ABORT_ERROR:    error      2                   ;Exit with error 2
1372                  .page
1373                  ;***** OFF:     Power down routines
1374                                  .global    OFF
1375                                  .extern    PLAY_DEAD
1376
1377  0319            OFF:            display    OFFDIS
1381  031D    14 00                   CALL       PLAY_DEAD
1382  031F    24 BE                   JMP        BLOW
1383
1394                  ;***** CHTEST:  Check if charger off.
1385                                  .global    CHTEST
1386  0321    83      CHTEST:         RET
1387
1388  0322            BATLOW:         error      1
1392
1393  0326                            end
```

Lines Assembled : 1393          Assembly Errors : 0

```
                2500 A.D. 8748 Macro Assembler   -  Version 4.02a
                -------------------------------------------------

Input  Filename : j4int.src
                          Output Filename : j4int.obj 326                                 .list on
327                                 .external           ADTOT
328                                 .comment \
329                                 ***** Interrupt TIMER / HEATER desccription
330
331                                 Crystal frequency       : XTAL=6 MHZ
332                                 1 TIMER count           : 3/6 * 5 * 32 = 80 us
333                                 Software Timer rate     : 40 hardware TIMER counts = 3.2 ms
334                                 Refresh period          : 4 characters * 3.2 ms = 12.8 ms
335                                 PWM HEATER resolution   : 3.2ms
336                                 PWM period              : 3.2ms
337
338                                 Heater Description:
339
340                                 The average HEATER voltage is varied by use of PWM.  The amount of on time
341                                 (in 3.2ms resolution ) is dependent on the required power and the battery volts
342                                 As the batteries die the PW must be increased to account for the voltage loss.
343                                 The on time is determined from a Look-up table.  HEATER is calculated by fore
344                                 ground software.
345                                                 heater on    heater off
346                                                 -----------
347                                                |            |             |
348                                                 --------      ---------------
349                                                '- HEATER->'<-TICK-HEATER->'
350                                                '----- TICK ------------->
351
352
353                                 \
354         FFD8            TICK         EQU       -40             ;Interrupt counter.
355
356         0007                         ORG       7H
357         0007   04 00                 JMP       TIINT           ;Interrupt vector
358         0060            .CODE
359         0000                         .ORG      00
360                                      .global   TIINT,TICK
361         0000   D5      TIINT:        SEL       RB1
362         0001   AA                    MOV       ASAVE,A         ;Save accumulator
363         0002
364         0002   FC                    MOV       A,INT32         ;40 interrupts ???
365         0003   C6 1F                 JZ        HTR_OFF         ;Yes - turn heater off
366
367         0005            I32ON:       djnz      HEATER,HTRON    ;HEATER = 0 ???
372         000A                         heater_off              ;Yes - Turn heater off
375
376         000C   23 D8                 MOV       A,#TICK         ;Reload Interrupt counter
377         000E   62                    MOV       T,A
378         000F   04 32                 JMP       SETADF          ;Set AD flag, display refresh
379
380                         ;***** HTRON: Redefine a new interrupt that between 0 and 3.2ms that will
381                         ;             turn the heater back off.  Indicate this interrupt with the
382                         ;             heater flag HTR_FLG
383
384
385         0011            HTRON:       heater_on               ;Turn HEATER on
388         0013   37                    CPL       A
389         0014   17                    INC       A
390         0015
391         0015   62                    MOV       T,A             ;INT COUNT(3.2ms) = TICK - HEATER
392         0016   C7                    DEC       A
393         0017   37                    CPL       A
394         0018   03 D8                 ADD       A,#TICK         ;Timing to turn HEATER off
395         001A   AD                    MOV       HTROFF,A
396         001B   BC 00                 MOV       INT32,#0        ;Turn HEATER off next interrupt
397         001D
398         001D   04 36                 JMP       I32_EXIT        ;Not enough time to read AD
399
400                         ;***** HTROFF: HYCYCLE  gives the fraction of the Interrupt time in a delay
401                         ;              loop.  It is used to increase the resolution of the HEATER to
402                         ;              greater then 80us
403
404         001F   FD      HTR_OFF:      MOV       A,HTROFF        ;Value that takes next INT to 3.2ms
405         0020   62                    MOV       T,A             ;Stored when the HEATER was turned on
406
407         0021   B8 4E   HTR_DELAY:    MOV       R0,#HCYCLE      ;Get partial delay
408         0023   F0                    MOV       A,@R0
409         0024   A9                    MOV       R1,A
410         0025   19                    INC       R1
411
412         0026   E9 26   HD1:          DJNZ      R1,HD1
413         0028                         heater_off
416
417         002A   BC FF                 MOV       INT32,#0FFH     ;Set INT32 flag
418         002C                         set       ADFLAG,0FFH     ;Set AD flag
422         0030   04 27                 JMP       TRET            ;Common exit
423         0032
```

```
424  0032                SETADF:     set    ADFLAG,0FFH      ;Set AD flag
425
426  0036                ADC_EXIT:
427                      .page
428  ****;    .* OPTIONS:
429                      ;            Scan diode option before digit is changed
430                      ;            Digit drivers are slower than DS8863N.
431                      ;            OPTION is an image the 4 option diodes - Diode in = '
432
433                      ;***** OPTIONS:
434  0036  B8 56         OPTIONS:    MOV    R0,#OPTION
435  0038  0A                        IN     A,P2
436  0039  53 20                     ANL    A,#DIODES        ;Diode found this scan ???
437  003B  96 48                     JNZ    DIODE            ;Yes - set option
438
439  003D  FB            NO_DIODE:   MOV    A,DIGIT          ;No - Disable option in option mask
440  003E  37                        CPL    A                ;Get DIGIT scanner
441  003F  AB                        MOV    DIGIT,A
442  0040  F0                        MOV    A,@R0
443  0041  5B                        ANL    A,DIGIT          ;Mask off option using DIGIT scanner
444  0042  A0                        MOV    @R0,A            ;Store option
445  0043
446  0043  FB                        MOV    A,DIGIT          ;Store current DIGIT scanner
447  0044  37                        CPL    A
448  0045  AB                        MOV    DIGIT,A
449  0046  04 4B                     JMP    OPTION_EXIT
450
451  0048  F0            DIODE:      MOV    A,@R0            ;Set appropriate option bit
452  0049  4B                        ORL    A,DIGIT
453  004A  A0                        MOV    @R0,A
454  004B                OPTION_EXIT:
455                      .page
456  ****;  .  ** REFRESH_DISPLAY:
457                      ;Refreshes the display and updates the DIGIT scanner.
458                      ;Digit scanner moves through D0-D3 of port selecting one of the four digits
459                      ;or one of the four option diodes
460
461  004B                REFRESH_DISPLAY:
462
463  004B  FB                        MOV    A,DIGIT          ;Get DIGIT scanner
464  004C  77                        RR     A                ;Shift to the right
465  004D  53 0F                     ANL    A,#00001111B     ;Do not shift past D3
466  004F  AB                        MOV    DIGIT,A          ;Save
467  0050  96 9E                     JNZ    DIGIT_STROBE
468  0052  23 08                     MOV    A,#00001000B     ;Reset scan
469  0054  AB                        MOV    DIGIT,A          ;Start new scan and update timer ;***** CLOCK:
                      ;            TSEC  - decremented every second
                      ;            TFRAC - decremented every 12.8ms
                      ;            Clock stopped: TSEC=TFRAC=0
                      ;            If TFRAC = 0 then exit 0055  B8 20         CLOCK:      MOV    R0,#TFRAC        ;Get TFRAC
     0057  F0                        MOV    A,@R0
     0058  C6 6A                     JZ     CLOCK_EXIT       ;Exit if Zero
     005A
     005A  07                        DEC    A                ;TFRAC=TFRAC-1
     005B  A0                        MOV    @R0,A
     005C  96 6A                     JNZ    CLOCK_EXIT       ;Exit if not 0

005E  B0 4E                     MOV    @R0,#TCAL        ;TFRAC=TCAL
     0060  18                        INC    R0               ;Point to TSEC
     0061  F0                        MOV    A,@R0            ;TSEC=TSEC-1
     0062  07                        DEC    A
     0063  A0                        MOV    @R0,A 0064  17                        INC    A                ;Time up ???
     0065  96 6A                     JNZ    CLOCK_EXIT       ;no - exit
     0067
     0067  A0                        MOV    @R0,A            ;Yes - zero TFRAC and TSEC
     0068  C8                        DEC    R0               ;TFRAC=TSEC=0
     0069  A0                        MOV    @R0,A 006A                CLOCK_EXIT:
                        .page
                      **;* *** SEND_PICTURE:  Send a picture by activating port while SEND is high
                                              Decrement SEND every 12.8ms
     006A                            get    SEND
     006D  C6 7B                     JZ     SEND_EXIT
     006F
     006F  07                        DEC    A
     0070  A0                        MOV    @R0,A 0071  C6 77                     JZ     DISABLE_SEND
     0073             send_on
     0075  04 7B                     JMP    SEND_EXIT 0077                DISABLE_SEND: send_off              ;No - Disable send
     0079                            lamp_off
     007B                SEND_EXIT:

.page
```

```
533                   ***** ; * AUDIO:
534                         ;   Here every 12.8 ms. BEEP time update
535                         ;
536                         ;           BEEP= 0FFH       Continuous beep
537                         ;           BEEP= 0          No Beep
538                         ;           Beep time = BEEP * 12.8ms
539   007B
540   007B  B8 55         AUDIO:    MOV     R0,#BEEP        ;Get BEEP timer
541   007D  F0                      MOV     A,@R0           ;BEEP = 0 ???
542   007E  C6 8C                   JZ      BPOFF           ;Yes - Beeper off,exit
543
544   0080  17                      INC     A               ;BEEP = FF
545   0081  C6 89                   JZ      BPON            ;Yes - Beeper on
546   0083
547   0083  07                      DEC     A               ;Decrement BEEP duration counter
548   0084  07                      DEC     A
549   0085  A0                      MOV     @R0,A           ;and store remaining time
550   0086  C6 8C                   JZ      BPOFF           ;If BEEP= 0 then turn beeper off
551
552   0089         BPON:    beeper_on                       ;Turn beeper on
555   008A  04 8E                   JMP     AUDIO_EXIT
556
557   008C         BPOFF:   beeper_off                      ;Turn beeper off
560
561   008E         AUDIO_EXIT:
562
563
564
565
566                  ;***** DIGIT_STROBE:              ;Strobe output according to digit
567
568   008E  FB       DIGIT_STROBE:   MOV     A,DIGIT
569   008F  98 F0                    ANL     BUS,#\DMSK      ;Clear digit strobe
570   0091  99 00                    ANL     P1,#0           ;Clear segment driver port
571   0093  B8 23                    MOV     R0,#SEG3        ;First segment
572   0095  72 AA                    JB3     D3
573   0097  18                       INC     R0
574   0098  52 A6                    JB2     D2
575   009A  18                       INC     R0
576   009B  32 A2                    JB1     D1
577   009D  18                       INC     R0
578   009E  88 08      D0:           ORL     BUS,#DM0        ;Digit 0
579   00A0  04 AC                    JMP     DIG2
580   00A2  88 04      D1:           ORL     BUS,#DM1        ;Digit 1
581   00A4  04 AC                    JMP     DIG2
582   00A6  88 02      D2:           ORL     BUS,#DM2        ;Digit 2
583   00A8  04 AC                    JMP     DIG2
584   00AA  88 01      D3:           ORL     BUS,#DM3        ;Digit 3
585   00AC  F0         DIG2:         MOV     A,@R0           ;Get segment DATA
586   00AD  39                       OUTL    P1,A            ;Latch it on PORT 1
587                  .page
588                  ****; * PRES_TIME:
589                      ;Here every 3.2 ms
590                      ;The PS timer consists of 2 a byte incrementing counter.
591
592   00AE  0A       PRES_TIME:   IN      A,P2
593   00AF  53 80                 ANL     A,#PSMSK
594   00B1  96 BC                 JNZ     PLOW
595   00B3  FE       PHIGH:        MOV     A,PSTLOR
596   00B4  03 01                 ADD     A,#1
597   00B6  AE                    MOV     PSTLOR,A
598   00B7  E6 BF                 JNC     PEXIT
599   00B9  1F                    INC     PSTHIR
600   00BA  04 BF                 JMP     PEXIT
601   00BC  27       PLOW:        CLR     A
602   00BD  AE                    MOV     PSTLOR,A
603   00BE  AF                    MOV     PSTHIR,A
604   00BF           PEXIT:
605                  .page
606                  ****; * POWER_OFF
607                      ; Check for power down request
608                      ;
609   00BF  46 C7                 JNT1    STILON
610   00C1  88 20    PWROFF:  ORL     BUS,#RELAY       ;Raise relay if charger input=0
611   00C3  99 00              ANL     P1,#BLANK        ;Clear the segment (lower current)
612   00C5  89 40              ORL     P1,#DECPT        ;Leave decimal point on
613   00C7           STILON:
614   00C7  FA       TRET:    MOV     A,ASAVE          ;RESTORE ACCUMULATOR
615   00C8  93                 RETR
616
617
618
619
620                  ;***** ADINT:              Here when AD interrupts DJNZ R3 loop
621                  ;                          Disable the Interrupts, Clear A and return R4 comp
622   00C9
623                  .global ADINT
624   00C9  15       ADINT:   DIS     I
625   00CA  FB                MOV     A,R3
626   00CB  37                CPL     A
627   00CC  AC                MOV     R4,A
628   00CD  27                CLR     A
629   00CE  93       PE0:     RETR
630   00CF                    end Lines Assembled : 630          Assembly Errors : 0
```

J4UTIL.SRC - J4 subroutines
Test Program

```
            2500 A.D. 8748 Macro Assembler  -  Version 4.02a
            -----------------------------------------------

Input  Filename : j4util.src
                    Output Filename : j4util.obj

330                             .list on
331   0000                      .code
332   0000                      .global    ADTOT,SUB16,MUL16,DIV16,BEEPSR,ONESEC,ERRPT,HTRADF,ADD16,SUB16R
333                             .extern    OFF,CHTEST
334   0000
335                        ;***** HTRADJ:          Adjust heater duty cycle
336                        ;
337                        ;        Input:        Heater voltage, 250 = 10V
338                        ;        Output: HEATER modified
339                        ;                HCYCLE modified
340                        ;        Temp:   All Regs
341                        ;
342                        ;Description:
343                        ;                HTRLST contains pairs of data, timer counts and cycles
344                        ;                Top of list: HEATER of 2.5V or AD of 125
345                        ;                End of list: HEATER of 4.4V or AD of 220
346   0000
347                             .global    HTRADJ
348
349   0000  BA 07       HTRADJ:    MOV     R2,#RCHAN     ;Read reference channel
350   0002  B9 48                  MOV     R1,#RTOTAL
351   0004  14 3E                  CALL    ADTOT
352
353   0006  BA 00                  MOV     R2,#ZCHAN     ;Read zero
354   0008  B9 46                  MOV     R1,#ZTOTAL
355   000A  14 3E                  CALL    ADTOT
356
357   000C  BA 03       HTRADF:    MOV     R2,#HCHAN     ;Entry point for faster routine
358   000E  B9 44                  MOV     R1,#XTOTAL
359   0010  14 3E                  CALL    ADTOT
360
361   0012  14 71                  CALL    ADCALC        ;125 < Result <250
362
363   0014  B9 4E                  MOV     R1,#HCYCLE    ;Zero HCYCLE
364   0016  B1 00                  MOV     @R1,#0
365   0018  C9                     DEC     R1            ;Point to HEATER
366
367   0019  FD                     MOV     A,R5          ;Result > 255 ???
368   001A  96 28                  JNZ     HEXIT         ;Yes - exit
369
370   001C  FC                     MOV     A,R4
371   001D  03 13                  ADD     A,#19         ;Diode drop compensation
372
373   001F  03 83                  ADD     A,#-125       ;Base of list is 125
374   0021  F2 2B                  JB7     TOOLOW        ;If passed base then too low
375   0023  AA                     MOV     R2,A          ;Save pointer
376                                                       pair
377   0024  03 A1                  ADD     A,#-95        ;95 pair of data available
378   0026  F2 31                  JB7     HLOOP
379                                                       ;Exit if past list
380   0028  B1 05       HEXIT:     MOV     @R1,#5        ;Default value is low
381   002A  83                     RET
382
383   002B  03 32       TOOLOW:    ADD     A,#50
384   002D  F2 28                  JB7     HEXIT         ;Very low  less than 75.
385   002F  BA 00                  MOV     R2,#0         ;Top of HTRLST if low but not very low
386   0031  FA          HLOOP:     MOV     A,R2          ;Return the offset AD count
387   0032  E7                     RL      A             ;*2
388   0033  03 00                  ADD     A,#HTRLST
389   0035  AA                     MOV     R2,A          ;Save R2 pointing to HEATER value
390   0036  E3                     MOVP3   A,@A          ;Get the HEATER value
391   0037  A1                     MOV     @R1,A         ;Store at HEATER
392   0038  19                     INC     R1            ;Point to HCYCLE and store from list
393   0039  1A                     INC     R2
394   003A  FA                     MOV     A,R2
395   003B  E3                     MOVP3   A,@A
396   003C  A1                     MOV     @R1,A
397   003D  83                     RET
398   003E
399                             .page
400                        ;***** ADTOT:     AD totalizing routine
401   003E
402                        ;        Input:  R2      Address of channel to be converted
403                        ;        Output: R1      Points to two byte total
404                        ;        Temp:   R4      Count result ,0=min, 255=max
405                        ;                R5      Sample counter
406                        ;                R0,R3
407                        ;                R6,R7   Stores total
408   003E
409                        ;Description    25 AD samples are taken in approx 80 ms
410                        ;                Total stored at R1
411                        ;                Uses MC14443
412                        ;                Processor decrements a counter while waiting for interrupt
413                        ;                The compliment of the count is the result
414
```

```
415  003E  BD 19            ADTOT:       MOV    R5,#25       ;Sample counter
416  0040  27                            CLR    A            ;CLR total
417  0041  AE                            MOV    R6,A
418  0042  AF                            MOV    R7,A
419  0043
420  0043               ADCONV:
421  0043  B8 43                         MOV    R0,#ADFLAG   ;Clear flags
422  0045  B0 00                         MOV    @R0,#0
423
424  0047  F0          AD1:             MOV    A,@R0         ;Wait for timer to set flag
425  0048  C6 47                         JZ     AD1          ;There is now time for an AD
426
427  004A  23 E0                         MOV    A,#INPUTS    ;Select channel
428  004C  4A                            ORL    A,R2
429  004D  3A                            OUTL   P2,A
430                  .page
431               ;**--** CAP_CHARGE:   Wait 250us to charge up the timing capacitor
432                  ;                  2.5us/cycle, therfore 250us = 100 cycles
433                  ;                  Max HEATER = 19*80 =1520us
434                  ;                  Max cap discharge = 2.5*255 =1275us
435                  ;                  Therefore app 400 us to charge AD cap
436
437  004E               CAP_CHARGE:  ramp_end              ;Start ramp
440  0050  BB 31                         MOV    R3,#(100-2)/2; ;2 cycles
441  0052  EB 52       CAP1:            DJNZ   R3,CAP1       ;2 cycles
442
443  0054  BB 00                         MOV    R3,#0         ;Clear counter
444  0056  27                            CLR    A             ;Use as interrupt or time out flag
445  0057  37                            CPL    A
446  0058  05                            EN     I             ;Enable Interrupt
447  0059                               ramp_start            ;Start ramp
450  005B
451  005B  EB 5B       DISCHARGE:       DJNZ   R3,DISCHARGE  ;Interrupt ???
452  005D  15                            DIS    I
453  005E  C6 62                         JZ     AD_TOTAL      ;Yes - set by interrupt if A = 0
454  0060  BC FF                         MOV    R4,#0FFH      ;No - treat as overflow if A=FF
455
456  0062  FC          AD_TOTAL:        MOV    A,R4          ;Add LSB to TOTAL
457  0063  6E                            ADD    A,R6
458  0064  AE                            MOV    R6,A
459  0065  FF                            MOV    A,R7
460  0066  13 00                         ADDC   A,#0          ;MSB if Carry
461  0068  AF                            MOV    R7,A
462  0069
463  0069  ED 43                         DJNZ   R5,ADCONV     ;25 samples done ??? - No continue
464  006B  FE                            MOV    A,R6          ;Yes - store total
465  006C  A1                            MOV    @R1,A
466  006D  19                            INC    R1
467  006E  FF                            MOV    A,R7
468  006F  A1                            MOV    @R1,A
469  0070  83                            RET
470               .page
471               ;** = ADCALC:        AD calculation
472                 ;                  Using XTOTAL, ZTOTAL, RTOTAL calculated the compensated
473                 ;                  unknown voltage. (2.50V = 500)
474                 ;     Output: R4,R5
475                 ;
476                 ;     Reading =(XTOTAL-ZTOTAL)*500 /(RTOTAL-ZTOTAL)
477                 ;
478                                     .global ADCALC
479
480  0071  B8 48       ADCALC:          MOV    R0,#RTOTAL    ;RTOTAL IN R6,R7
481  0073  F0                            MOV    A,@R0
482  0074  AE                            MOV    R6,A
483  0075  19                            INC    R0
484  0076  F0                            MOV    A,@R0
485  0077  AF                            MOV    R7,A
486  0078
487  0078  B8 46                         MOV    R0,#ZTOTAL    ;ZTOTAL IN R2,R3
488  007A  F0                            MOV    A,@R0
489  007B  AA                            MOV    R2,A
490  007C  19                            INC    R0
491  007D  F0                            MOV    A,@R0
492  007E  AB                            MOV    R3,A
493  007F  54 8A                         CALL   SUB16         ;RESULT IN R2,R3
494  0081  B8 59                         MOV    R0,#RSPAN     ;STORE AT RSPAN
495  0083  FA                            MOV    A,R2
496  0084  A0                            MOV    @R0,A
497  0085  18                            INC    R0
498  0086  FB                            MOV    A,R3
499  0087  A0                            MOV    @R0,A
500  0088  B8 44                         MOV    R0,#XTOTAL    ;XTOTAL IN R6,R7
501  008A  F0                            MOV    A,@R0
502  008B  AE                            MOV    R6,A
503  008C  18                            INC    R0
504  008D  F0                            MOV    A,@R0
505  008E  AF                            MOV    R7,A
506  008F  B8 46                         MOV    R0,#ZTOTAL    ;ZTOTAL IN R2,R3
507  0091  F0                            MOV    A,@R0
508  0092  AA                            MOV    R2,A
509  0093  18                            INC    R0
510  0094  F0                            MOV    A,@R0
511  0095  AB                            MOV    R3,A
512  0096  54 8A                         CALL   SUB16         ;RESULT IN R2,R3
513  0098  FB                            MOV    A,R3          ;CHECK RESULT FOR NEGATIVE
514  0099  37                            CPL    A
515  009A  F2 A0                         JB7    ISPOS         ;BYPASS IF POSITIVE
```

```
516   009C   BA 00                 MOV     R2,#0          ;ELSE MAKE IT 0
517   009E   BB 00                 MOV     R3,#0
518   00A0   BC F4       ISPOS:    MOV     R4,#<500       ;500 IN R4,R5
519   00A2   BD 01                 MOV     R5,#>500
520   00A4   54 49                 CALL    MUL16          ;RESULT (R2-R5)
521   00A6   FD                    MOV     A,R5           ;MOVE IT UP TO (R4-R7)
522   00A7   AF                    MOV     R7,A
523   00A8   FC                    MOV     A,R4
524   00A9   AE                    MOV     R6,A
525   00AA   FB                    MOV     A,R3
526   00AB   AD                    MOV     R5,A
527   00AC   FA                    MOV     A,R2
528   00AD   AC                    MOV     R4,A
529   00AE   B8 59                 MOV     R0,#RSPAN      ;FROM BEING SAVED
530   00B0   F0                    MOV     A,@R0
531   00B1   AA                    MOV     R2,A
532   00B2   18                    INC     R0
533   00B3   F0                    MOV     A,@R0
534   00B4   AB                    MOV     R3,A
535   00B5   54 04                 CALL    DIV16          ;RESULT IN R4,R5
536   00B7   83                    RET
537                     .page
538
539                     ;***** BINSEG:    16 bit binary to BCD pattern
540                     ;
541                     ;          Input: A        Lower 8 bits
542                     ;                 R2       Upper 8 bits
543                     ;                 R0       Pointer to packed BCD string
544                     ;          Temp:  R1,R3
545                     ;                 R4,R5
546   00B8
547                     ;          From Microcontrollers handbook PGS 3-76
548   00B8
549          0002       XA         reg      R2
550          0003       COUNT      reg      R3
551          0004       ICNT       reg      R4
552          0003       DIGPR      reg      3
553          0005       TEMP1      reg      R5
554
555                                .global  BINSEG
556
557   00B8   B8 58      BINSEG:    MOV      R0,#PACK      ;Result of first step in PACK, PACK+1
558   00BA   28                    XCH      A,R0
559   00BB   A9                    MOV      R1,A
560   00BC   28                    XCH      A,R0
561   00BD   BC 03                 MOV      ICNT,#DIGPR
562   00BF   B1 00      BCDCOA:    MOV      @R1,#00
563   00C1   19                    INC      R1
564   00C2   EC BF                 DJNZ     ICNT,BCDCOA
565   00C4   BB 10                 MOV      COUNT,#16
566   00C6   97         BCDCOB:    CLR      C
567   00C7   F7                    RLC      A
568   00C8   2A                    XCH      A,XA
569   00C9   F7                    RLC      A
570   00CA   2A                    XCH      A,XA
571   00CB   28                    XCH      A,R0
572   00CC   A9                    MOV      R1,A
573   00CD   28                    XCH      A,R0
574   00CE   BC 03                 MOV      ICNT,#DIGPR
575   00D0   AD                    MOV      TEMP1,A
576   00D1   F1         BCDOC:     MOV      A,@R1
577   00D2   71                    ADDC     A,@R1
578   00D3   57                    DA       A
579   00D4   A1                    MOV      @R1,A
580   00D5   19                    INC      R1
581   00D6   EC D1                 DJNZ     ICNT,BCDCOC
582   00D8   FD                    MOV      A,TEMP1
583   00D9   F6 DE                 JC       BCDCOD
584   00DB   EB E6                 DJNZ     COUNT,BCDCOB
585   00DD   97                    CLR      C
586   00DE              BCDCOD:
587                     .page
588
589                     ;          THE BCD DATA IS NOW TIGTHLY PACKED INTO 2 BYTES AT PACK,PACK+1
590                     ;          LSB AT PACK, MSB AT PACK+1.
591                     ;          THE FOLLOWING WILL LOOSELY PACK IT IN PACK TO PACK+3
592                     ;          LSB AT PACK, MSB AT PACK+3.
593                     ;          R0 POINTS TO THE TIGHTLY PACKED SOURCE.
594                     ;          R1 POINTS TO THE LOOSELY PACKED DESTINATION.
595                     ;          R3 AND R4 ARE USED AS COUNTERS.
596                     ;
597
598   00DE   B8 59                 MOV      R0,#PACK+1    ;MSB
599   00E0   B9 5B                 MOV      R1,#PACK+3    ;MSB
600   00E2   BC 02                 MOV      R4,#2         ;INNER LOOP
601   00E4   BB 02      OUTER:     MOV      R3,#2         ;OUTER LOOP
602   00E6   F0                    MOV      A,@R0         ;GET BCD FROM TIGHTLY PACKED SOURCE
603   00E7   47         INNER:     SWAP     A
604   00E8   B1 00                 MOV      @R1,#0        ;CLEAR DESTINATION
605   00EA   31                    XCHD     A,@R1         ;FILL IN NIBBLE
606   00EB   C9                    DEC      R1            ;NEXT DESTINATION
607   00EC   EB E7                 DJNZ     R3,INNER
608   00EE   C9                    DEC      R0
609   00EF   EC E4                 DJNZ     R4,OUTER
610
611                     ;          CONVERT THE LOOSELY PACKED 4 BYTES TO SEGMENT PATTERNS
612                     ;          SEG3     SEG2      SEG1     SEG0
613                     ;          PACK+3   PACK+2    PACK+1   PACK+0
```

```
614
615   00F1   BA 14                           MOV       R2,#4           ;COUNTER
616   00F3   B8 23                           MOV       R0,#SEG3        ;POINTER
617   00F5   B9 5B                           MOV       R1,#PACK-3      ;POINTER
618   00F7   F1           SEG:               MOV       A,@R1           ;GET BCD
619   00F8   03 C0                           ADD       A,#-SEGPAT      ;ADD THE SEGMENT PATTERN BASE ADDRESS
620   00FA   E3                              MOVP3     A,@A            ;GET THE SEGMENT PATTERN INTO A
621   00FB   A0                              MOV       @R0,A           ;AND INTO THE SEGMENT PATTERN BUFFER
622   00FC   18                              INC       R0              ;NEXT SEGMENT
623   00FD   C9                              DEC       R1              ;NEXT BCD
624   00FE   EA F7                           DJNZ      R2,SEG
625                              .page
626
627                              ;***** DISPLAY_TYPE:     Decode the type of display format specified
628                              ;                        by option diodes
629
630                              ;Using D1,D0 of OPTION: 0=USA, SOUTH AFRICA
631                              ;                       1=CANADA, ENGLAND, AUSTRAILIA
632                              ;                       2=GERMANY, FINLAND
633                              ;                       3= NOT USED
634
635   0100                       DISPLAY_TYPE:
636   0100                                   get       OPTION          ;Read OPTION
640   0103   53 03                           ANL       A,#00000011B    ;Lower 2 bits only
641   0105   C6 0E                           JZ        USASA
642   0107   07                              DEC       A
643   0108   C6 1C                           JZ        CANENG
644   010A   07                              DEC       A
645   010B   C6 2F                           JZ        GRMFIN
646   010D   83                              RET                       ;3=normal ,4 digit display
647
648
649
650                              ;***** USASA:   Display for USA " .0XX"
651                              ;               Blank out MSD if zero and add a decimal
652   010E
653   010E                       USASA:      get       SEG3
657   0111   D3 BB                           XRL       A,#NUM0
658   0113   96 17                           JNZ       USASA0          ;JUMP IF NOT A 0
659   0115   B0 00                           MOV       @R0,#BLANK      ;ELSE BLANK IT
660   0117   F0           USASA0:            MOV       A,@R0           ;ADD THE DECIMAL POINT
661   0118   43 40                           ORL       A,#DECPT
662   011A   A0                              MOV       @R0,A
663   011B   83                              RET
664
665                              .page                           English
666                              *****:  CANENG:   Display for Canada and English   "XX"
667                              :                 No decimal points with leading blanks
668   011C
669   011C   B8 22        CANENG:            MOV       R0,#SEG3-1
670   011E   18           CE0:               INC       R0              ;NEXT SEGMENT
671   011F   F8                              MOV       A,R0
672   0120   03 DA                           ADD       A,#-SEG0        ;CHECK FOR SEG0
673   0122   96 25                           JNZ       CE1
674   0124   83                              RET                       ;RET IF SEG0
675   0125   F0           CE1:               MOV       A,@R0           ;GET SEGMENT PATTERN
676   0126   D3 BB                           XRL       A,#NUM0
677   0128   C6 2B                           JZ        CE2
678   012A   83                              RET                       ;RET IF NOT A ZERO
679   012B   B0 00        CE2:               MOV       @R0,#BLANK      ;ELSE MAKE IT A BLANK
680   012D   24 1E                           JMP       CE0
681   012F   24 31        GRMFIN:            JMP       GFJMP           ;OVER THE PAGE BOUNDARY
682   0131                       PE1:
683   0131
684
685
686
687                              ;***** GFJMP:   Display for Germany and Finland " 0.XX"
688                              ;               Leading blank with decimal between digits 2 and 3
689
690   0131   B8 23        GFJMP:             MOV       R0,#SEG3
691   0133   F0                              MOV       A,@R0
692   0134   D3 BB                           XRL       A,#NUM0
693   0136   96 3A                           JNZ       GF1             ;JUMP IF SEGMENT NOT A ZERO
694   0139   B0 00                           MOV       @R0,#BLANK      ;ELSE A 0
695   013A   18           GF1:               INC       R0
696   013B   F0                              MOV       A,@R0           ;GET NEXT DIGIT
697   013C   43 40                           ORL       A,#DECPT        ;ADD THE DECIMAL POINT
698   013E   A0                              MOV       @R0,A
699   013F   83                              RET
700   0140
701                              .page                           characters
702                              ****:   DISPLY:  Display a sequence of 4 chars  stored on page 3
703
704                              ;       Input:  R1      page 3 address of 4 characters to display
705                              ;       Output: R0      points to last segment buffer
706
707                              .global DISPLY
708   0140   B8 22        DISPLY:            MOV       R0,#SEG3-1
709   0142   BA 04                           MOV       R2,#4           ;COUNTER
710   0144   18           DIS1:              INC       R0              ;POINT TO NEXT PATTERN
711   0145   F9                              MOV       A,R1            ;POINT ACC TO NEXT PATTERN
712   0146   E3                              MOVP3     A,@A
713   0147   A0                              MOV       @R0,A           ;INTO THE BUFFER
714   0148   19                              INC       R1              ;POINT TO NEXT PATTERN
715   0149   EA 44                           DJNZ      R2,DIS1
716   014B   83                              RET
717                              .page
```

```
718                    ;****   ERRPT:          Entry point for all of the errors
719
720   014C  34 6A      ERRPT:         CALL    ERRDIS       ;Display error code
721   014E                             set     HEATER,00
725
726   0150  54 A7                     CALL    ONESEC       ;TIMER=1 SEC
727   0154  B9 20                     MOV     R1,#TFRAC
728   0156  14 00      BTL0:          CALL    CHTEST
729   0158  F1                        MOV     A,@R1        ;Time up ???
730   0159  96 56                     JNZ     BTL0         ;No -keep waiting
731
732   015B  54 AF                     CALL    BEEPSR       ;BEEP
733   015D  19                        INC     R1
734   015E
735   015E  B1 0A                     MOV     @R1,#10      ;TIMER=10 SEC
736   0160  C9                        DEC     R1
737   0161  B1 01                     MOV     @R1,#1
738   0163  14 00      BTL:           CALL    CHTEST
739   0165  F1                        MOV     A,@R1        ;Time up ???
740   0166  96 63                     JNZ     BTL          ;No - keep waiting
741   0168  04 00                     JMP     OFF          ;Turn J4 off
742   016A
743
744
745                    ;***** ERRDIS:          Display error code
746                    ;
747                    ;           Input:  R3     Error number
748
749                    .global ERRDIS
750
751   016A  B9 DA      ERRDIS:        MOV     R1,# ERRPAT
752   016C  34 40                     CALL    DISPLY       ;R0 - Last segment buffer
753   016E  23 C0                     MOV     A,#!SEGPAT
754   0170  6B                        ADD     A,R3
755   0171  E3                        MOVP3   A,@A
756   0172  A0                        MOV     @R0,A
757   0173  83                        RET
758                    .subtitle Test Program
759                    .page J4UTIL.SRC    - J4 subroutines
Test Program 760                    ;****   TEST_PROGRAM:
761
762                    ;Test conditions:
763                    ;                    Display    : VREF = 25 =5600
764                    ;                    Test Point : High - Display CAL POT 0166
765                    ;                    Reed Switch: If closed heater control is active, display sensor
766                    ;                    PS closed  : Turn off HEATER
767   0174
768                    .global TEST_PROGRAM
769   0174             TEST_PROGRAM:  relay_on
772
773   0176             TEST1:         set     HEATER,00    ;Turn HEATER off
777   017A
778   017A  27                        CLR     A            ;Clear discharge timer
779   017B  B9 4B                     MOV     R1,#SCNT
780   017D  F1                        MOV     A,@R1
781   017E  19                        INC     R1
782   017F  F1                        MOV     A,@R1
783   0180
784   0180  BA 07                     MOV     R2,#RCHAN    ;Read reference channel
785   0182  B9 48                     MOV     R1,#RTOTAL   ;Write AD reading for reference
786   0184  14 3E                     CALL    ADTOT        ;Read AD
787   0186
788   0186  24 D9                     JMP     TESTC        ;Yes - read CAL POT
789
790   0188  FF                        MOV     A,R7         ;Reference returned in R6,R7 by ADTOT
791   0189  AA                        MOV     R2,A
792   018A  FE                        MOV     A,R6         ;Convert for displaying
793   018B  14 B8                     CALL    BINSEG
794                    .page
795                    ;***   = WAIT:
796   018D             WAIT           timer   0,TCAL/8     ;Wait 1/8 sec
802   0194  0A         WAIT:          IN      A,P2         ;PS closed ???
803   0195  53 80                     ANL     A,#PSMSK
804   0197  96 9D                     JNZ     WAIT         ;No - keep on waiting
805
806   0199             set            HEATER,0             ;Yes - turn HEATER off
810   019D  B8 20      WAIT1:         MOV     R0,#TFRAC
811   019F  F0                        MOV     A,@R0
812   01A0  96 94                     JNZ     WAIT
813
914   01A2  0A                        IN      A,P2         ;Reed switch closed ???
915   01A3  53 40                     ANL     A,#REED
916   01A5  96 76                     JNZ     TEST1        ;No - continue current test
817   01A7
818   01A7  0A         HTRA:          IN      A,P2         ;PS closed ???
819   01A8  53 80                     ANL     A,#PSMSK
820   01AA  C6 AE                     JZ      HTRA1        ;Yes - HEATER off
821   01AC  14 00                     CALL    HTRADJ
822
923   01AE  34 FB      HTRA1:         CALL    MEASSF       ;Measure Sensor
924
```

```
825  01B0  FD              TESTD:      MOV     A,R5            ;Display R4,R5
826  01B1  AA                          MOV     R2,A
827  01B2  FC                          MOV     A,R4
828  01B3  14 B8                       CALL    BINSEG
829
830  01B5  B9 4B                       MOV     R1,#SCNT        ;SCNT=SCNT+1
831  01B7  11                          INC     @R1
832  01B8  F1                          MOV     A,@R1
833  01B9  D3 87                       XRL     A,#CNTCAL
834  01BB  19                          INC     R1              ;increment minutes on counter MINON
835  01BC  96 C3                       JNZ     DICHARGE_BAT
836
837  01BE  C9                          DEC     R1
838  01BF  B1 00                       MOV     @R1,#0           ;SCNT=0
839  01C1  19                          INC     R1
840  01C2  11                          INC     @R1             ;MINON=MINON +1 increment minutes on
841                  .page
                     DICHARGE_BAT:
842  01C3  36 94                       JT0     WAIT            ;??? - No monitor sensor  Test Low
843  01C5  F1                          MOV     A,@R1           ;Yes - Display discharge time till dead
844  01C6  BA 00                       MOV     R2,#0           ;A,R2 - minutes of battery discharge
845  01C8  14 B8                       CALL    BINSEG          ;Display time
846  01CA                  set         HEATER,0                ;Turn HEATER off
850  01CE              DB1:  set       BEEP,25                 ;Long BEEP
854
855  01D0  54 A7                       CALL    ONESEC
856  01D4  F0              DB2:        MOV     A,@R0           ;Wait one second
857  01D5  96 D4                       JNZ     DB2             ;One second over ???
858  01D7  24 CE                       JMP     DB1             ;Yes - BEEP every second
859  01D9
860          0087          CNTCAL      EQU     135
861  01D9
862  01D9  BA 00           TESTC:      MOV     R2,#ZCHAN       ;DISPLAY CAL. POT READING
863  01DB  B9 46                       MOV     R1,#ZTOTAL
864  01DD  14 3E                       CALL    ADTOT
865  01DF  BA 02                       MOV     R2,#CCHAN
866  01E1  B9 44                       MOV     R1,#XTOTAL
867  01E3  14 3E                       CALL    ADTOT
868  01E5  BA 07                       MOV     R2,#RCHAN
869  01E7  B9 48                       MOV     R1,#RTOTAL
870  01E9  14 3E                       CALL    ADTOT
871  01EB  14 71                       CALL    ADCALC
872  01ED  24 B0                       JMP     TESTD
873                  .page
874              *****:   MEASS:       Measure senosr channel
875                          .global MEASS
876                          .global MEASSF
877
878  01EF  BA 07           MEASS:      MOV     R2,#RCHAN       ;REFERENCE
879  01F1  B9 48                       MOV     R1,#RTOTAL
880  01F3  14 3E                       CALL    ADTOT
881  01F5  BA 00                       MOV     R2,#ZCHAN       ;ZERO
882  01F7  B9 46                       MOV     R1,#ZTOTAL
883  01F9  14 3E                       CALL    ADTOT
884  01FB  BA 01           MEASSF:     MOV     R2,#SCHAN       ;SENSOR
885  01FD  B9 44                       MOV     R1,#XTOTAL
886  01FF  14 3E                       CALL    ADTOT
887  0201  14 71                       CALL    ADCALC
888  0203  83                          RET
889                  .page
890              *****:   DIV16:       Divide 32 bit number by 16 bit number - unsigned
891  0204
892                  ;    Input:   R7,R6,R5,R4     Dividend (LSB in R4)
893                  ;             R3,R2           Divisor  (LSB in R4)
894                  ;    Output:  R5,R4           Quotient (MSB in R5)
895                  ;             R7,R6           Remainder(MSB in R7)
896                  ;
897  0204  FA              DIV16:      MOV     A,R2            ;Negate divisor in preparation for div
898  0205  37                          CPL     A
899  0206  03 01                       ADD     A,#01
900  0208  AA                          MOV     R2,A
901  0209  FB                          MOV     A,R3
902  020A  37                          CPL     A
903  020B  13 00                       ADDC    A,#0
904  020D  AB                          MOV     R3,A
905
906  020E  54 13                       CALL    DIV1            ;Divide 3 MSB of dividend
907  0210  54 13                       CALL    DIV1            ;Divide whats left
908  0212  83                          RET
909                  .page                                     dividend
910              *****:   DIV1:        ;Divide 24 bit dividend by 16 bit divisor
911  0213
912                  ;    Input:   R7,R6,R4        Dividend (MSB in R7)
913                  ;             R3,R2           Negated divisor (MSB in R3)
914                  ;    Output:  R5,R4           Quotient (MSB in R5)
915                  ;             R7,R6           Remainder (MSB in R6)
916
917  0213  FC              DIV1:       MOV     A,R4            ;Get 3RD MSB into A
918  0214  2D                          XCH     A,R5            ;LSB of dividend into R5
919  0215  BC 08                       MOV     R4,#8           ;Set loop count
920
921  0217  97              DIV2:       CLR     C               ;Shift 3 MSB of dividend once
922  0218  F7                          RLC     A               ;3RD byte
923  0219  2E                          XCH     A,R6
924  021A  F7                          RLC     A
925  021B  2E                          XCH     A,R6            ;2ND MSbyte
926  021C  2F                          XCH     A,R7            ;MSbyte
```

```
927   021D   F7                           RLC     A
928   021E   2F                           XCH     A,R7
929   021F   F6 34                        JC      DIV3        ;If Dividend > Divisor then subtract
930
931
932   0221   2B           SUB:            XCH     A,R3        ;Dividend > Divisor ???
933   0222   A9                           MOV     R1,A
934   0223   2B                           XCH     A,R3
935   0224   2A                           XCH     A,R2
936   0225   A8                           MOV     R0,A
937   0226   2A                           XCH     A,R2
938   0227   54 77                        CALL    ADD16
939   0229   E6 32                        JNC     NOTOK       ;Yes - skip subtraction
940   022B
941   022B   17                           INC     A           ;No  - subtract divisor from dividend
942   022C   28                           XCH     A,R0        ;    - quotient = 1
943   022D   AE                           MOV     R6,A
944   022E   28                           XCH     A,R0
945   022F   29                           XCH     A,R1
946   0230   AF                           MOV     R7,A
947   0231   29                           XCH     A,R1
948   0232   44 43        NOTOK:          JMP     DIV4        ;Go to end of loop
949                       .page
950
951   0234   17           DIV3:           INC     A
952   0235   2B                           XCH     A,R3        ;Setup subtraction
953   0236   A9                           MOV     R1,A
954   0237   2B                           XCH     A,R3
955   0238   2A                           XCH     A,R2
956   0239   A9                           MOV     R0,A
957   023A   2A                           XCH     A,R2
958   023B   54 77                        CALL    ADD16
959
960   023D   28                           XCH     A,R0        ;Dividend = result of subtraction
961   023E   AE                           MOV     R6,A
962   023F   28                           XCH     A,R0
963   0240   29                           XCH     A,R1
964   0241   AF                           MOV     R7,A
965   0242   29                           XCH     A,R1
966   0243   EC 17        DIV4:           DJNZ    R4,DIV2
967   0245   AC                           MOV     R4,A
968   0246   97                           CLR     C
969   0247   A7                           CPL     C
970   0248   83                           RET
971                       .page
972                ****;  * MUL16:                8 bit * 16 bit multiplication
973   0249
974                       :       Input:  R5,R4           Multiplicand
975                       :               R3,R2           Multiplier
976                       :       Output: R5,R4,R3,R2     Result
977
978                       :Description:   Longhand multiplication
979                       :               2 bytes of multiplicand are multiplied by each byte of
980                       :               multiplier. The 4 byte result is added together
981   0249
982   0249   54 62        MUL16:          CALL    BMULT       ;mplcnd * LSbyte of multiplier
983
984   024B   AF                           MOV     R7,A        ;Pack MSbyte of product
985   024C   F9                           MOV     A,R1        ;Pack 2nd MSbyte of product
986   024D   AE                           MOV     R6,A
987   024E   FA                           MOV     A,R2
988   024F   2B                           XCH     A,R3
989   0250   AA                           MOV     R2,A
990
991   0251   54 62                        CALL    BMULT       ;mltplcnd * MSbyte of multiplier
992   0253   2A                           XCH     A,R2        ;LSbyte of result for addition
993   0254   A8                           MOV     R0,A
994   0255   54 77                        CALL    ADD16
995   0257   FA                           MOV     A,R2
996   0258   E6 5B                        JNC     AROUND      ;MSbyte of 2nd product
997   025A   17                           INC     A           ;Adds overflow to MSbyte
998
999   025B   AD           AROUND:         MOV     R5,A        ;MSbyte in R5
000   025C   F9                           MOV     A,R1        ;2ND MSbyte in R4
001   025D   AC                           MOV     R4,A
002   025E   F8                           MOV     A,R0        ;3RD MSbyte in R3
003   025F   2B                           XCH     A,R3
004   0260   AA                           MOV     R2,A        ;LSbyte in R2
005   0261   83                           RET
006                       .page
007                ****;  * BMULT:                8 bit * 16 bit multiplication
008                       :
009                       :       Input:  R5,R4           :Multiplicand
010                       :               R2              :Multiplier
011                       :               A,R1,R2         :Result
012   0262
013   0262   27           BMULT:          CLR     A           ;Clear registers
014   0263   A9                           MOV     R1,A
015   0264   B8 09                        MOV     R0,#9       ;LOOP COUNT+1
016   0266   97                           CLR     C
017   0267   67           MUL1:           RRC     A           ;Rotate all 3 bytes of product and
018   0268   29                           XCH     A,R1        ;bring multiplier bit into Carry
019   0269   67                           RRC     A
020   026A   29                           XCH     A,R1
021   026B   2A                           XCH     A,R2
022   026C   67                           RRC     A
023   026D   2A                           XCH     A,R2        ;Multiplier bit =1 ???
```

```
024
025   026E   E6 74              JNC     MUL2            ;No - do not add to product
026   0270   29                 XCH     A,R1            ;Yes- add mltiplend to product
027   0271   6C                 ADD     A,R4
028   0272   29                 XCH     A,R1
029   0273   7D                 ADDC    A,R5
030   0274   E8 67     MUL2:    DJNZ    R0,MUL1
031   0276   83                 RET
032                             .page
033
034          ;***** ADD16:      Adds two unsigned 16 bit numbers
035
036                   ;         Input:  R7,R6           Addend  (MSbyte in R7)
037                   ;                 R1,R0           Augen   (MSbyte in R1)
038                   ;         Result: R0,R1           Result  MSbyte IN R1)
039   0277
040   0277   28       ADD16:    XCH     A,R0            ;GET LSBYT OF AUGEN
041   0278   6E                 ADD     A,R6            ;ADD IT TO LSB OF ADDEN
042   0279   28                 XCH     A,R0            ;STORE RESULT
043   027A   29                 XCH     A,R1            ;GET MSBYT OF AUGEN
044   027B   7F                 ADDC    A,R7            ;ADD IT TO MSBYT OF ADDEN AND LAST CARRY
045   027C   29                 XCH     A,R1            ;STORE RESULT IN R3
046   027D   83                 RET
047                             .page                   SUB16 below
048          ;***** SUB16R:     16 bit subtraction using SUB below but setting
049                   ;                                 up registers form pointers R0,R1
050   027E
051                   ;         R3,R2 = (R0)-(R1)
052
053                   ;         INPUT   R0 points to LB of Minuend
054                   ;                 R1 points to LB of Subtrahend
055                   ;         OUTPUT  R2,R3 result
056
057                   ;         IF (R0) = R1, then      C is set
058                   ;                                 otherwise C is cleared
059   027E   F0       SUB16R:   MOV     A,@R0
060   027F   AE                 MOV     R6,A
061   0280   18                 INC     R0
062   0281   F0                 MOV     A,@R0
063   0282   AF                 MOV     R7,A
064
065   0283   F1                 MOV     A,@R1
066   0284   AA                 MOV     R2,A
067   0285   19                 INC     R1
068   0286   F1                 MOV     A,@R1
069   0287   AB                 MOV     R3,A
070
071   0288   C8                 DEC     R0              ;Return R0,R1 unchanged
072   0289   C9                 DEC     R1
073
074                   ;         Equation (R3,R2)=(R7,R6)-(R3,R2)
075                   ;         Input:  R7,R6           Minuend (MSB in R7)
076                   ;                 R3,R2           Subtrahend (MSB in R3)
077                   ;         Output: R3,R2           Result (MSB in R3)
078
079   028A   FA       SUB16:    MOV     A,R2            ;Negate subtrahend lower byte
080   028B   37                 CPL     A
081   028C   03 01              ADD     A,#1
082   028E   AA                 MOV     R2,A
083   028F
084   028F   FB                 MOV     A,R3            ;Negate higher byte
085   0290   37                 CPL     A
086   0291   13 00              ADDC    A,#0
087   0293   AB                 MOV     R3,A
088
089   0294   FA                 MOV     A,R2            ;Add lower bytes
090   0295   6E                 ADD     A,R6
091   0296   AA                 MOV     R2,A
092   0297
093   0297   FB                 MOV     A,R3            ;Add higher bytes
094   0298   7F                 ADDC    A,R7
095   0299   AB                 MOV     R3,A
096   029A   83                 RET
097                             .page
098          ;***** R45R67:     Move REG R4,R5 to R6,R7
099                             .global R45R67
100   029B   FD       R45R67:   MOV     A,R5
101   029C   AF                 MOV     R7,A
102   029D   FC                 MOV     A,R4
103   029E   AE                 MOV     R6,A
104   029F   83                 RET
105   02A0
106          ;***** SAV45:      Save R4,R5 at R0
107                             .global SAV45
108   02A0   FC       SAV45:    MOV     A,R4
109   02A1   A0                 MOV     @R0,A
110   02A2   18                 INC     R0
111   02A3   FD                 MOV     A,R5
112   02A4   A0                 MOV     @R0,A
113   02A5   C8                 DEC     R0
114   02A6   83                 RET
115
116
117          ;***** ONESEC:     Initialize TIMER to 1 second
118
119   02A7            ONESEC:   timer   1,1
120   02AE   83                 RET
```

```
 126
 127
 128
 129                          ;***** BEEPS:     Beep for one second
 130
 131  02AF  B8 55      BEEPSR:     MOV    R0,#BEEP
 132  02B1  B0 0C                  MOV    @R0,#10
 133  02B3  83                     RET
 134
 135  02B4
 136                        .page
1137                   ;*** ** PLAY_DEAD:     Unit shuts display/A   but keeps HEATER alive at some
1138                   ;                        steady state value
1139                   ;                      Routine returns when PS closes
1140                   ;                      Routine displays rotating BAR
1141  02B4
1142                                    .global PLAY_DEAD
1143  02B4            PLAY_DEAD:   set    HEATER,DEAD_HEATER
1147  02B8  18                    INC    R0
1148  02B9  B0 01                 MOV    @R0,01
1149
1150  02BB                        display DEAD
1154  02BF            PD1:        timer  1,1                  ;TIMER = 1
1160
1161  02C6  0A        PD2:        IN     A,P2                 ;PS = closed ???
1162  02C7  53 80                 ANL    A,#PSMSK
1163  02C9  96 CC                 JNZ    PD3                  ;No - continue
1164  02CB  83                    RET                         ;Yes- return
1165
1166  02CC  F0        PD3:        MOV    A,@R0                ;TIMER = 0 ???
1167  02CD  96 C6                 JNZ    PD2                  ;No - wait for time up
1168
1169  02CF  54 D3                 CALL   ROTATE               ;Rotate display
1170  02D1  44 BF                 JMP    PD1
1171
1172
1173                   ;***** ROTATE:      Rotate the display so that SEG3 ends up in SEG0
1174
1175
1176  02D3  B8 21     ROTATE:      MOV    R0,#SEG3-2           ;Rotate Display Characters
1177  02D5  B9 22                  MOV    R1,#SEG3-1
1178
1179  02D7  BA 04                  MOV    R2,#4                ;For n=1 TO 4
1180
1181  02D9  18        MORE_ROTATE: INC    R0
1182  02DA  19                     INC    R1
1183
1184  02DB  F1                     MOV    A,@R1                ;SEGn = SEG(n-1)
1185  02DC  A0                     MOV    @R0,A
1186
1187  02DD  EA D9                  DJNZ   R2,MORE_ROTATE       ;n=n-1, n= 0???
1188  02DF
1189  02DF                         get    SEG3-1               ;Rotate top of buffer to bottom
1193  02E2  A1                     MOV    @R1,A
1194  02E3  83                     RET
1195  02E4                         END Lines Assembled :  1195         Assembly Errors :   0

;***** J4DATA.SRC  Data assignments
;***** Start of Ram
         .ORG 1EH
         .ABSOLUTE BANK1:   :Start of BANK 1

PSTLO:    DS    1               ;P.S. LB - Not relocatable since this address
PSTHI:    DS    1               ;      HB - can be directly addresses by R6,R7

TFRAC:    DS    1               ;FRACtions of a sec (TCAL,SEC)
TSEC:     DS    1               ;SEConds
SEG_R:    DS    1               ;Used to rotate segments
SEG3:     DS    1               ;Segment buffer digit  3
SEG2:     DS    1               ;                      2
SEG1:     DS    1               ;                      1
SEG0:     DS    1               ;                      0

READY:    DS    1               ;# of SEC sensor is ready
RTIMER:   DS    1               ;Time to READY
ABCNT:    DS    1               ;ABORT counter S52:      DS    1               ;sample at 5.2   HB
S52H:     DS    1               ;                LB SP:       DS    1               ;Sample Pointer
SPAST:    DS    1               ;previous sample LB
SPASTH:   DS    1               ;                HB
SNOW:     DS    1               ;current sample  LB
SNOWH:    DS    1               ;                HB
RMAX:     DS    2               ;Max reading
RMIN:     DS    2               ;Min reading
READ:     DS    14              ;Baseline samples
```

```
ADFLAG:    DS    1             ;A/D ready flag
XTOTAL:    DS    2             ;25 AD readings
ZTOTAL:    DS    2             ;25 zero or ground AD readings
RTOTAL:    DS    3             ;25 reference AD readings
SCNT:      DS    1             ;FRACtion count for discharge
MINON:     DS    1             ;Minutes for above HEATER:    DS    1             ;Heater On time
HCYCLE:    DS    1             ;Heater Period
HTRSAV:    DS    1             ;Heater setting BLAST:     DS    1             ;Blast time
TUP:       DS    1             ;TIME of FOREVER LOOP
BLT10:     DS    1             ;Bias less then 10 flag SUSER:     DS    1             ;User CALibration pot LB
SUSERH:    DS    1             ;                     HB
BEEP:      DS    1             ;FF= constant beep, 0 = beeper off
OPTION:    DS    1             ;D0-D3 diode options
CAL:       DS    1             ;CAL mode flag FF= CAL
PACK:      DS    1             ;Temporary storage
RSPAN:     DS    1
TMP1:      DS    1
TMP2:      DS    1
TMP3:      DS    1
TMP4:      DS    1

SEND:      DS    2             ;Send signal timer @ 10.8ms

ENDRAM:          ;End of RAM
.page
   .relative

; HTRLST , must be on page 3 for addressing
;
; HEATER LIST starting at 1.5 V or AD = 105
;                      to 4.4 V or AD = 220

; First entry : HEATER , Hardware Interrupt counts @ 80us
; Second entry: HTRCYC , 0.5 * cycles ( 16 cycles = 80 us)
           .DATA
   ORG     300H HTRLST:    DB    18,9,18,3,17,15,17,10
           DB    17,6,17,2,16,13,16,9
           DB    16,5,16,2,15,14,15,10
           DB    15,6,15,3,14,15,14,12
           DB    14,9,14,5,14,2,13,15
           DB    13,12,13,9,13,6,13,3
           DB    13,0,12,13,12,11,12,8
           DB    12,6,12,3,12,0,11,14
           DB    11,12,11,9,11,7,11,5
           DB    11,2,11,0,10,14,10,12
           DB    10,10,10,8,10,6,10,4
           DB    10,2,10,0,9,14,9,12
           DB    9,11,9,9,9,7,9,5
           DB    9,4,9,2,9,0,8,15
           DB    8,13,8,12,8,10,8,9
           DB    8,7,8,6,8,4,8,3
           DB    8,1,8,0,7,15,7,13
           DB    7,12,7,11,7,10,7,8
           DB    7,7,7,6,7,5,7,4
           DB    7,3,7,1,7,0,6,15
           DB    6,14,6,13,6,12,6,11
           DB    6,10,6,9,6,8,6,7
           DB    6,6,6,5,6,4,6,3
           DB    6,2,6,1,6,0,6,0
;
SEGPAT:    DB    NUM0
           DB    NUM1
           DB    NUM2
           DB    NUM3
           DB    NUM4
           DB    NUM5
           DB    NUM7
           DB    NUM8
           DB    NUM9
.page
SEGTST:    DB    0FFH,0FFH,0FFH,0FFH       ;ALL SEGMENTS ON
BLOPAT:    DB    LETB,LCL,LETO,BLANK       ;BLO
ONPAT:     DB    NUM0,LETN,BLANK,BLANK     ;ON
ABTPAT:    DB    NUM0,LETN,BLANK,LETA      ;ON A
ERRPAT:    DB    LETE,LETR,LETR            ;ERRX
DASHPT:    DB    DASH,DASH,DASH,DASH       ;----
OFFDIS:    DB    LETO,LETH,BLANK,BLANK     ;OH
PASSPT:    DB    LETP,LETA,LETS,LETS       ;PASS
WARNPT:    DB    LETS,LETU,LETS,LETP       ;SUSP
FAILPT:    DB    LETF,LETA,LETI,LETL       ;FAIL
DEAD:      DB    BLANK,DECPT,BLANK,DECPT   ;Moving bar ;***** Alternate Register Names:

ASAVE            reg   R2           ;Accumulator save
DIGIT            reg   R3           ;Digit pattern for strobing displays
```

```
INT30          reg      R4              ;HEATER or timing
HTROFF         reg      R5              ;Balance of 3.2 ms
PSTLOR         reg      R6              ;Pressure switch timer  LB
PSTHIR         reg      R7              ;                       HB
;***** Definitions:

ZCHAN          EQU      0               ;Zero channel address
SCHAN          EQU      1               ;Sensor channel address
CCHAN          EQU      2               ;User calibration channel address
HCHAN          EQU      3               ;HEATER channel address
RCHAN          EQU      7               ;VREF channel address ;***** Operating parameters
TCAL           EQU      78              ;Timer calibration for 1 sec . 1000/12.8ms
BLOW_TIME      EQU      1719            ;Blow time = time;sec;/0.0032
NUMSAM         EQU      7               ;Number of samples for a stable baseline
RANGE          EQU      2               ;Range of baseline samples for READY
DEAD_HEATER    EQU      5               ;Steady state value of HEATER when PLAY_DEAD
HTR_PURGE      EQU      10              ;Heater value during display time
disp           EQU      40              ;Length of time BAC is displayed
.page
;*****     I/O LINES:

;***** DATA BUS:

DMSK           EQU      00001111B       ;Digit strobes
DM3            EQU      00000001B       ;DB0
DM2            EQU      00000010B       ;DB1
DM1            EQU      00000100B       ;DB2
DM0            EQU      00001000B       ;DB3
RAMPST         EQU      00010000B       ;Ramp start
RELAY          EQU      00100000B       ;Relay
BEEPER         EQU      01000000B       ;Beeper
;***** PORT 1

;P17           OUT      SEGMENT c
;P16           OUT           "   D.P.
;P15           OUT           "   f
;P14           OUT           "   a
;P13           OUT           "   b
;P12           OUT           "   g
;P11           OUT           "   d
;P10           OUT           "   e

;***** PORT 2

INPUTS         EQU      11100000B       ;Port 2 mask
PSMSK          EQU      10000000B       ;Pressure Switch
REED           EQU      01000000B       ;Reed Switch
DIODES         EQU      00100000B       ;Diodes
LAMP           EQU      00010000B       ;Test input
SEND_B         EQU      00001000B       ;SEND port

;***** TEST INPUTS

;T0            IN       POWER OFF=0
;T1            IN       BATTERY LOW=0
;INT           A/D COMPARATOR OUTPUT, ACTIVE LOW

.page
;*****     Segment Definitions

LETA           EQU      10111101B       ;Letter A
LETB           EQU      10100111B       ;   "   B
LETC           EQU      00110011B       ;   "   C
LETE           EQU      00110111B       ;   "   E
LETF           EQU      00110101B       ;   "   F
LETH           EQU      10101101B       ;   "   H
LETI           EQU      10001000B       ;   "   I
LETl1          EQU      00000001B       ;   "   l
LETL           EQU      00100011B       ;   "   L
LCL            EQU      00100001B       ;   "   l
LETN           EQU      10000101B       ;   "   N
LETO           EQU      10000111B       ;   "   O
LETP           EQU      00111101B       ;   "   P
LETR           EQU      00000101B       ;   "   R
LETT           EQU      00100111B       ;   .T
LETS           EQU      10110110B       ;   "   S
LETU           EQU      10101011B       ;   "   U
DECPT          EQU      01000000B       ;DECIMAL POINT
BLANK          EQU      00000000B       ;BLANK
DASH           EQU      00000100B       ;DASH "-"
NUM0           EQU      10111011B
NUM1           EQU      10001000B
NUM2           EQU      00011111B
NUM3           EQU      10011111B
NUM4           EQU      10101100B
NUM5           EQU      10110110B
NUM6           EQU      10110111B
NUM7           EQU      10011000B
NUM8           EQU      10111111B
NUM9           EQU      10111110B
BAR            EQU      10001000B
```

```
.page
;***** Macros:
timer           MACRO   SEC,PSEC        ;Load secs and frac for use by TIMER
                MOV     R0,#TSEC
                MOV     @R0,SEC
                DEC     R0
                MOV     @R0,PSEC
                ENDM heater_on       MACRO                   ;Turn HEATER on
                ANL     BUS,#\HTRMSK
                ENDM heater_off      MACRO                   ;Turn HEATER off
                ORL     BUS,#HTRMSK
                ENDM beeper_on       MACRO                   ;Turn BEEPER on
                ANL     BUS,#\BEEPER
                ENDM beeper_off      MACRO                   ;Turn BEEPER off
                ORL     BUS,#BEEPER
                ENDM relay_on        MACRO                   ;Turn RELAY on
                ANL     BUS,#\RELAY
                ENDM relay_off       MACRO                   ;Turn RELAY off
                ORL     BUS,#RELAY
                ENDM ramp_start      MACRO                   ;Start ramp for AD
                ORL     BUS,#RAMPST
                ENDM ramp_end        MACRO                   ;Turn ramp off for AD
                ANL     BUS,#\RAMPST
                ENDM send_on         MACRO                   ;Enable send
                ORL     P2,#SEND_B
                ENDM send_off        MACRO                   ;Disable send
                ANL     P2,#\SEND_B
                ENDM lamp_on         MACRO                   ;Turn lamp on
                ORL     P2,#LAMP
                ENDM
lamp_off        MACRO                   ;Turn lamp off
                ANL     P2,#\LAMP
                ENDM
cjnz            MACRO   C1,C2           ;Compare to zero jump not zero
                MOV     R0,#C1
                MOV     A,@R0
                JNZ     C2
                ENDM cjz             MACRO   C3,C4           ;Compare to zero jump if zero
                MOV     R0,#C3
                MOV     A,@R0
                JZ      C4
                ENDM set             MACRO   S1,S2           ;Set memory location with data
                MOV     R0,#S1
                MOV     @R0,S2
                ENDM get             MACRO   G1              ;Get data from memory into A
                MOV     R0,#G1
                MOV     A,@R0
                ENDM error           MACRO   E1              ;Display error code and power down
                MOV     R3,#E1
                CALL    EPPPT
                ENDM load_display    MACRO   LD1             ;Point display at LD1
                MOV     R1,#LD1
                ENDM display         MACRO   DP1             ;Display string
                MOV     R1,#DP1
                CALL    DISPLY
                ENDM
```

What is claimed is:

1. A monitoring station for use in a remote confinement system, said station comprising:
a telecommunications camera connectable to a central station by way of a communications link, said camera defining an image field viewed by said camera;
mechanical locating means for locating a person at a location within said image field such that the face of the person substantially fills said image field;
means for generating a trip signal in response to a flow of breath from the person when the person is located by said locating means at said location, and
control means responsive to said trip signal for enabling an image of the person to be viewed at said central station.

2. A monitoring station for use in a remote confinement system, said station comprising:
(a) a telecommunications camera connectable to a central station by way of a communications link, said camera defining an image field viewed by said camera;
(b) mechanical locating means for locating a person at a specific location within said image field such that the face of the person substantially fills said image field;
(c) an alcohol breath tester for determining the blood alcohol content of a person, said tester including means responsive to the delivery of a breath sample thereinto for generating a first trip signal, and
(d) control means responsive to said trip signal for enabling an image of the person to be viewed at said central station whereby viewing of background images at said central station is avoided.

3. The monitoring station of claim 2 wherein said locating means comprises means for maintaining a distance between said camera and a person using said breath tester appropriate to ensure said first image is substantially in focus.

4. The monitoring station of claim 2 wherein said locating means comprises an arm supporting said breath tester.

5. The monitoring station of claim 4 wherein said arm is connected to said camera.

6. The monitoring station of claim 4 further comprising base means associated with said camera, at least a portion of said arm being selectively, receivable within said base in a retracted position and extendable from said base in an extended position.

7. The monitoring station of claim 6 wherein said extended position of said arm effectively locates the head of a person using said breath tester to ensure that said first image at least one of:
(i) is substantially in focus, and
(ii) substantially fills said image field.

8. The monitoring station of claim 7 further comprising limit switch means operably connected to said camera to sense the position of said arm and permit said camera to form an image only when said arm is in said extended position.

9. The monitoring station of claim 2 wherein said camera has a depth of field of more than about five feet.

10. The monitoring station of claim 9 wherein said depth of field of said camera includes at least a portion of both said specific location and said background.

11. The monitoring station of claim 2 further comprising means for generating a second trip signal after said first trip signal has been generated to initiate at least one of, forming and transmitting a second image.

12. The monitoring station of claim 11 further comprising visually readable display means for indicating alcohol content, said display being disposed within said field of view so that said second image includes said display as well as said person.

13. The monitoring station of claim 12 wherein said display means further comprises means for indicating at least one of the following conditions:
(i) that the breath tester is prepared to receive a breath sample;
(ii) that a breath test is in progress, and
(iii) that a breath test has been aborted.

14. The monitoring station of claim 12 further comprising illumination means directed toward at least a portion of said image field, said illumination means adapted to be lighted when forming said first image so that said person is clearly visible therein and dimmed when forming said second image so that said display is clearly visible therein.

15. The monitoring station of claim 11 wherein said alcohol breath tester includes breath sample validity ensuring means for requiring said breath sample to be delivered as a substantially continuous, uninterrupted flow of breath over a predetermined interval of time as a required condition for generating said second trip signal.

16. The monitoring station of claim 15 wherein said breath sample validity ensuring means includes breath flow sensing means and timing means responsive to said breath flow sensing means.

17. The monitoring station of claim 15 wherein said second trip signal is generated after said predetermined interval elapses.

18. The monitoring station of claim 2 further comprising illumination means to illuminate at least a portion of said image field in response to said first trip signal.

19. A monitoring system comprising:
(a) a central station;
(b) at least one monitoring station connectable to said central station by way of a communications link, said monitoring station including:
(i) a telecommunications camera defining an image field viewed by said camera;
(ii) means for locating a person at a location within said image field such that the face of the person substantially fills said image field, and
(iii) breath flow responsive actuating means for generating a trip signal in response to a flow of breath from the person when the person is located by said locating means at said location, and
(c) control means responsive to said trip signal for enabling an image of the person to be viewed at said central office.

20. The system of claim 19 wherein said actuating means forms part of an alcohol breath tester for determining the blood alcohol content of a person blowing breath into said breath tester.

21. A monitoring system comprising:
(a) a central station;
(b) at least one monitoring station connectable to said central station by way of a communication link, said monitoring station including:
(i) an alcohol breath tester for determining the blood alcohol content of a person, said tester including means responsive to the delivery of a breath sample thereinto for generating a first trip signal, and (ii) a telecommunications camera connected to said breath tester and having a field of view directed generally toward said tester, said telecommunications camera requiring receipt of said first trip signal to initiate at least one of, forming and transmitting, a first image of a person using said breath tester.

22. The system of claim 21 further comprising:
mechanical locating means for locating the head of a person using said breath tester such that the face of the person substantially fills said image field whereby transmission of background images is avoided.

23. The system of claim 22 wherein said locating means comprises means for maintaining a distance between said camera and a person using said breath tester appropriate to ensure said first image is substantially in focus.

24. The system of claim 22 wherein said locating means comprises an arm supporting said breath tester.

25. The system of claim 24 wherein said arm is connected to said camera.

26. The system of claim 25 further comprising base means associated with said camera, at least a portion of said arm being, selectively, receivable within said base in a retracted position and extendable from said base in an extended position.

27. The system of claim 26 wherein said extended position of said arm effectively locates the head of a person using said breath tester to ensure that said first image at least one of:
(i) is substantially in focus, and
(ii) substantially fills said image field.

28. The system of claim 27 further comprising limit switch means operably connected to said camera to sense the position of said arm and permit said camera to form an image only when said arm is in said extended position.

29. The system of claim 21 further comprising means for generating a second trip signal after said first trip signal has been generated to initiate at least one of, forming and transmitting a second image.

30. The system of claim 29 further comprising visually readable display means for indicating alcohol content, said display being disposed within said field of view so that said second image includes said display as well as said person.

31. The system of claim 30 wherein said display means further comprises means for indicating at least one of the following conditions:
(i) that the breath tester is prepared to receive a breath sample;
(ii) that a breath test is in progress, and
(iii) that a breath test has been aborted.

32. The system of claim 30 further comprising illumination means directed toward at least a portion of said image field, said illumination means adapted to be lighted when forming said first image so that said person is clearly visible therein and dimmed when forming said second image so that said display is clearly visible therein.

33. The system of claim 29 wherein said alcohol breath tester includes breath sample validity ensuring means for requiring said breath sample to be delivered as a substantially continuous, uninterrupted flow of breath over a predetermined interval of time as a required condition for generating said second trip signal.

34. The system of claim 33 wherein said breath sample validity ensuring means includes breath flow sensing means and timing means responsive to said breath flow sensing means.

35. The system of claim 29 wherein said second trip signal is generated after said predetermined interval elapses.

36. The system of claim 21 further comprising illumination means to illuminate at least a portion of said image field in response to said first trip signal.

37. A method for monitoring from a central station confinees confined at a remote location equipped with an alcohol breath tester for determining the blood alcohol content of a person based on a breath sample delivered into the tester and further equipped with a telecommunications camera connected to said central location by way of a communications link, said method comprising the steps of:
forming an image with the camera, said image including said person and the display of the breath tester, said image being formed in response to the delivery of breath into said tester, and
transmitting said first and second images to the central station by way of the communications link to determine:
(i) whether said person is a specified confinee who is present at the remote location, and
(ii) at least one of, the presence of alcohol in the person's breath and the concentration of alcohol in the person's blood.

38. The method of claim 37 further comprising the step of, mechanically locating said breath tester in a predetermined position with respect to the camera, said position being selected such that the image of at least an identifiable portion of a person blowing breath into said breath tester substantially fills the image field viewed by the camera whereby the transmission of background images is avoided.

39. The method of claim 37 further comprising the step of, mechanically locating said breath tester in a predetermined position with respect to the camera, said position being selected such that the image of at least an identifiable portion of a person blowing breath into said breath tester together with the display of the breath tester substantially fills the image field viewed by the camera whereby the transmission of background images is avoided.

40. A method for monitoring from a central station confinees at a remote location equipped with an alcohol breath tester for determining the blood alcohol content of a person based on a breath sample delivered into the tester and further equipped with a telecommunications camera connected to said central station by way of a communications link, said method comprising the steps of:
forming at least two successive images at the remote location using the camera, a first of said images including at least said person, a second of said images including at least the display of the tester, said first image being formed in response to the delivery of breath into said tester, said second image being formed subsequently to said first image following a time delay without further action required on the part of said person, and
transmitting said first and second images to the central station by way of the communications link to determine:
(i) whether said person is a specified confinee who is present at the remote location, and
(ii) at least one of, the presence of alcohol in the person's breath and the concentration of alcohol in the person's blood.

41. A monitoring station for use in a remote confinement system, said station comprising:
a telecommunications camera defining an image field viewed by said camera;
mechanical means for locating the head of a person at a specific location within said image field such that the face of the person substantially fills said image field, and
actuating means connected to said camera, said actuating means being responsive to a flow of breath from said person to generate a trip signal, said telecommunications camera requiring receipt of said trip signal to initiate at least one of, forming and transmitting an image of said person.

42. A monitoring station for use in a remote confinement system, said station comprising:
(a) an alcohol breath tester for determining the blood alcohol content of a person, said tester including means responsive to the delivery of a breath sample thereinto for generating a first trip signal, and
(b) a telecommunications camera connected to said breath tester, said camera defining an image field viewed by said camera directed generally toward said tester, said telecommunications camera requiring receipt of said first trip signal to initiate at least one of, forming and transmitting, a first image of a person using said breath tester.

43. The monitoring station of claim 42 further comprising:
mechanical locating means for locating a person operating said breath tester such that at least one of, the face and head, of the person substantially fills said image field whereby transmission of background images is avoided.

44. The monitoring station of claim 43 wherein said locating means comprises means for maintaining a distance between said camera and a person using said breath tester appropriate to ensure said first image is substantially in focus.

45. The monitoring station of claim 43 wherein said locating means comprises an arm supporting said breath tester.

46. The monitoring station of claim 45 wherein said arm is connected to said camera.

47. The monitoring station of claim 45 further comprising base means associated with said camera, at least a portion of said arm being, selectively, receivable within said base in a retracted position and extendable from said base in an extended position.

48. The monitoring station of claim 47 wherein said extended position of said arm effectively locates the head of a person using said breath tester to ensure that said first image at least one of:
(i) is substantially in focus, and
(ii) substantially fills said image field.

49. The monitoring station of claim 48 further comprising limit switch means operably connected to said camera to sense the position of said arm and permit said camera to form an image only when said arm is in said extended position.

50. The monitoring station of claim 42 further comprising means for generating a second trip signal after said first trip signal has been generated to initiate at least one of, forming and transmitting a second image.

51. The monitoring station of claim 50 further comprising visually readable display means for indicating alcohol content, said display being disposed within said field of view so that said second image includes said display as well as said person.

52. The monitoring station of claim 51 wherein said display means further comprises means for indicating at least one of the following conditions:
(i) that the breath tester is prepared to receive a breath sample;
(ii) that a breath test is in progress, and
(iii) that a breath test has been aborted.

53. The monitoring station of claim 51 further comprising illumination means directed toward at least a portion of said image field, said illumination means adapted to be lighted when forming said first image so that said person is clearly visible therein and dimmed when forming said second image so that said display is clearly visible therein.

54. The monitoring station of claim 50 wherein said alcohol breath tester includes breath sample validity ensuring means for requiring said breath sample to be delivered as a substantially continuous, uninterrupted flow of breath over a predetermined interval of time as a required condition for generating said second trip signal.

55. The monitoring station of claim 54 wherein said breath sample validity ensuring means includes breath flow sensing means and timing means responsive to said breath flow sensing means.

56. The monitoring station of claim 54 wherein said second trip signal is generated after said predetermined interval elapses.

57. The monitoring station of claim 42 further comprising illumination means to illuminate at least a portion of said image field in response to said first trip signal.

58. A monitoring system comprising:
(a) a central station;
(b) at least one monitoring station connectable to said central station by way of a communications link, said monitoring station including:
(i) a telecommunications camera defining an image field viewed by said camera;
(ii) mechanical means for locating the head of a person at a location such that, at least one of, the face and head of the person substantially fills said image field, and
(iii) actuating means connected to said camera, said actuating means being responsive to a flow of breath to generate a trip signal, said telecommunications camera requiring receipt of said trip signal to initiate at least one of, forming and transmitting an image of said person to said central station.

59. A monitoring station for use in a remote confinement system, said station comprising:
a telecommunications camera connectable to a central office by way of a communications link, said camera defining an image field viewed by said camera;
mechanical locating means for locating a person at a location within said image field;
signal generating means operably connected to said mechanical locating means for enabling viewing said image field at said central location only if said person is located therein.

60. A monitoring station as in claim 59 wherein said signal generating means enables viewing of said image field only when the face of said person substantially fills said image field.

61. The monitoring station of claim 60 wherein said signal generating means is a breath flow responsive means.

62. The monitoring station of claim 59 wherein said signal generating means is a breath flow responsive means.

63. A monitoring station for use in a remote confinement system, said station comprising:
- a telecommunications camera connectable to a central office by way of a communications link, said camera defining an image field viewed by said camera, and
- means operably connected to said camera for generating a signal in response to a flow of breath from a person for enabling an image of the person to be viewed at said central office.

* * * * *

UNITED STATES PATENT AND TRADEMARK OFFICE
CERTIFICATE OF CORRECTION

PATENT NO. : 4,916,435
DATED : April 10, 1990
INVENTOR(S) : Kip L. Fuller

It is certified that error appears in the above-identified patent and that said Letters Patent is hereby corrected as shown below:

Col. 1, line 64, "fore" should be --for--.

Col. 5, line 15, delete "to".

Col. 5, line 31, "easiler" should be --easier--.

Col. 6, line 64, "confines" should be --confinees--.

Col. 6, line 67, "locaation" should be --location--.

Col. 10, line 15, "confines" should be --confinees--.

Col. 11, line 66, "48" should be --58--.

Col. 12, lines 15-16, "dsistance" should be --distance--.

Signed and Sealed this

Sixth Day of October, 1992

*Attest:*

DOUGLAS B. COMER

*Attesting Officer*     *Acting Commissioner of Patents and Trademarks*